United States Patent [19]

Okamura et al.

[11] Patent Number: 5,672,466
[45] Date of Patent: Sep. 30, 1997

[54] METHOD FOR FORMING AN IMAGE AND SILVER HALIDE PHOTOGRAPHIC LIGHT-SENSITIVE MATERIAL

[75] Inventors: Hisashi Okamura; Masaki Noro; Kazuhiko Matsumoto; Toshiki Taguchi, all of Minami-ashigara, Japan

[73] Assignee: Fuji Photo Film Co., Ltd., Kanagawa-ken, Japan

[21] Appl. No.: 605,780

[22] Filed: Feb. 22, 1996

[30] Foreign Application Priority Data

Feb. 24, 1995 [JP] Japan ................. 7-060110

[51] Int. Cl.$^6$ .............. G03C 1/42; G03C 1/498; G03C 5/30
[52] U.S. Cl. .............. 430/336; 430/505; 430/467; 430/483; 430/566; 430/351
[58] Field of Search .................. 430/505, 467, 430/483, 566, 336, 351

[56] References Cited

U.S. PATENT DOCUMENTS

| 3,076,721 | 2/1963 | Coles et al. . |
| 3,499,902 | 3/1970 | Coles et al. . |
| 3,751,255 | 8/1973 | Wilson et al. . |

FOREIGN PATENT DOCUMENTS

| 545491 | 6/1993 | European Pat. Off. . | |
| 565165 | 10/1993 | European Pat. Off. . | |
| 56-27132 | 3/1981 | Japan . | |
| 2-15856 | 4/1990 | Japan . | |
| 4-69776 | 11/1992 | Japan . | |
| 5-48901 | 7/1993 | Japan . | |
| 5-48902 | 7/1993 | Japan . | |
| 1141591 | 1/1969 | United Kingdom ............. | G03C 5/24 |
| 2056103 | 3/1981 | United Kingdom . | |

OTHER PUBLICATIONS

Justus Liebigs Annalen Der Chemie, vol. 651, 1962, Weinheim DE, pp. 89–101.

F.L. Scott et al., Journal of the Chemical Society, Perkin Transactions 1, Synthesis and Solvolysis . . . , pp. 2224–2231.

Research Disclosure 15,108.

Research Disclosure 15,127.

Research Disclosure 19,415.

*Primary Examiner*—Mark F. Huff
*Attorney, Agent, or Firm*—Birch, Stewart, Kolasch & Birch, LLP

[57] ABSTRACT

There is disclosed a silver halide photosensitive material and a method for forming an image, by the use of a color-developing agent of the type of carbonylhydrazone. The color-developing agent has satisfactory storage stability and capability for forming an image.

16 Claims, No Drawings

METHOD FOR FORMING AN IMAGE AND SILVER HALIDE PHOTOGRAPHIC LIGHT-SENSITIVE MATERIAL

FIELD OF THE INVENTION

The present invention relates to a novel color-developing agent for a silver halide photosensitive material, a silver halide photosensitive material containing the color-developing agent, and a method for forming an image by the use of a processing composition containing the color-developing agent.

BACKGROUND OF THE INVENTION

At the present time, commercially available silver halide color photographic material is a type of which a dye is formed by reaction of an oxidized aromatic primary amine with a color coupler. A color-developing agent is contained in a color-developing solution, and therefore a preservative is necessary to prevent deterioration of the developing solution. Further, it is necessary to process a waste solution safely. From this point of view, the development of light-sensitive materials in which the color-developing agent is incorporated has been pursued, including a heat-developing light-sensitive material developable by a heat process, and a light-sensitive material in which an image can be formed by processing with an alkaline aqueous solution. Further, the development of processing solutions containing a developing agent that is capable of rapid processing at a lower pH, and that therefore provides a minimized adverse influence on the environment, has been carried out.

In attempting to incorporate (build-in) the developing agent in a light-sensitive material, it is necessary to reconcile, at a high level, such needed but conflicting properties as long-term storage stability and sufficient image-forming capability.

In view of its quite poor storability, it is difficult to incorporate, in a light-sensitive material, an aromatic primary amine, which is a developing agent used in a silver halide color photographic material as an incorporated-type developing agent for a heat-developing light-sensitive material. Developed substitutes for the above-mentioned developing agent are sulfonamidephenol derivatives, as described in Research Disclosure (hereinafter abbreviated as "RD") No. 15108 and ibid. No. 15127; (p-hydroxyphenyl) sulfamine acid derivatives, 4-sulfoamino-5-pyrazolone derivatives or 4-sulfonamido-5-pyrazolone derivatives, and p-sulfonamidophenol derivatives or N,N-dialkyl-p-sulfonamidoaniline derivatives, as described respectively in JP-B ("JP-B" means examined Japanese patent publication) Nos. 69776/1992, 48901/1993, and 48902/1993; benzothiazolone hydrazone compounds or quinolone hydrazone compounds, as described in JP-B No. 15856/1990; and benzothiazolone sulfonylhydrazone compounds, as described in JP-A ("JP-A" means unexamined published Japanese patent application) No. 27132/1981, British patent 2056103B, and RD No. 19415. However, these compounds require processing at a high temperature for a long time, although they are generally good in storage stability. The processing is desired to be conducted at a low temperature for a short time, in view of the load to a processing apparatus and the stability of other elements constituting a light-sensitive material.

As an incorporated-type developing agent for a light-sensitive material developable with an alkaline aqueous solution free from the developing agent, sulfonylhydrazine compounds having a heterocyclic ring are described in EP 545,491A1 and EP 565,165A1. A light-sensitive material containing one of these developing agents is developable with a processing solution that has a pH value of 10.4 or 11.6 and that is free from the developing agent, and the material has an advantage that harmfulness induced by a waste solution is minor. However, such a light-sensitive material requires a long processing time. It is expected that a social problem of environmental contamination will become serious. Accordingly, the development of a light-sensitive material rapidly developable at a low pH value is desired, and this need also applies to a processing composition.

SUMMARY OF THE INVENTION

The present invention has improved the drawbacks of the prior arts as mentioned above. That is, an object of the present invention is to provide a method for forming an image by the use of a color-developing agent that is capable of rapidly forming an image under milder condition.

Another object of the present invention is to provide a silver halide light-sensitive material incorporating the above-described color-developing agent.

Still another object of the present invention is to provide a processing composition for the silver halide light-sensitive material incorporating the color-developing agent.

Other and further objects, features, and advantages of the invention will appear more evident form the following description.

DETAILED DESCRIPTION OF THE INVENTION

The above-described objects can be accomplished by the method for forming an image described below.

1. A method for forming an image, which method comprises developing a silver halide photographic light-sensitive material in the presence of a compound represented by the following general formula (A): general formula (A)

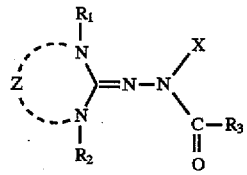

wherein $R_1$ and $R_2$ each represent an alkyl group, an aryl group, or a heterocyclic group; X represents a hydrogen atom, an acyl group, or a sulfonyl group; Z represents two or more non-metal atoms necessary to complete a 5- or 6-membered heterocyclic nucleus; $R_3$ represents an alkyl group, an aryl group, a heterocyclic group, —$OR_4$, or —$NR_5R_6$; and $R_4$, $R_5$, and $R_6$ each represent an alkyl group, an aryl group, or a heterocyclic group, with the proviso that $R_6$ may be a hydrogen atom.

2. A silver halide photographic light-sensitive material that comprises a compound represented by general formula (A) as illustrated above.

3. A silver halide photothermography light-sensitive material that comprises a compound represented by general formula (A) as illustrated above, wherein the compound forms an oxidation product at the portion where a latent image formed by an image-wise exposure to light is present, and wherein the oxidation product of the compound is capable of forming a dye image by reaction with a coupler.

4. A silver halide light-sensitive material capable of forming an image by an activator processing, which material comprises a compound represented by general formula (A) as illustrated above, wherein the compound forms an oxidation product at the portion where a latent image formed by an image-wise exposure to light is present, and wherein the oxidation product is capable of forming a dye image by reaction with a coupler.

5. An image-forming method that comprises developing an image-wise exposed silver halide light-sensitive material with a processing composition containing a compound represented by general formula (A) as illustrated above.

Further, preferred embodiments of the present invention include those described below.

6. An image-forming method that comprises developing a silver halide light-sensitive material in the presence of a compound represented by general formula (A) as illustrated above, which compound forms an oxidation product at the portion where a latent image formed by an image-wise exposure to light is present, and which oxidation product is capable of forming a dye image by reaction with a coupler.

7. A silver halide light-sensitive material comprising a compound represented by general formula (A) as illustrated above, which compound forms an oxidation product at the portion where a latent image formed by an image-wise exposure to light is present, and which oxidation product is capable of forming a dye image by reaction of the oxidation product with a coupler.

As a result of investigation of photographic properties with regard to various compounds prepared, in order to create a color-developing agent that has high image-forming properties that are adequate to achieve the above-described objects, it has been found that the compound represented by general formula (A) specifically solves the above-described problems. Advantages attained by an image-forming method that comprises using a compound represented by general formula (A) as a color-developing agent, are as follows.

(1) A heat-developable light-sensitive material is capable of forming an image by processing at a low temperature for a short time, (2) A light-sensitive material for an activator processing is capable of forming an image by the use of a processing solution having a low pH value, and (3) An image can be formed by processing a silver halide light-sensitive material with a processing solution containing a compound represented by general formula (A), as a color-developing agent at a low pH and for a short time.

Further, the storage stability achieved by the use of a compound represented by general formula (A), which is incorporated in a light-sensitive material (photographic material), is superior to previous incorporated-type developing agents having high activity.

$R_1$, $R_2$, $R_3$, X, and Z with respect to the compound represented by general formula (A) as illustrated above, for use in the present invention, are described in detail below.

$R_1$ and $R_2$ each represent an alkyl group (e.g. a straight-chain or branched alkyl group, an aralkyl group, an alkenyl group, an alkynyl group, a cycloalkyl group, or a cycloalkenyl group, having from 1 to 32 carbon atom(s)), an aryl group, or a heterocyclic ring group (the heterocyclic ring is, for example, a 5- or 6-membered saturated or unsaturated heterocyclic ring containing at least one of hetero atoms selected from an oxygen atom, a nitrogen atom, and a sulfur atom. The kind and number of the hetero atom that constitutes the ring may be one or more, respectively), which may be substituted with a substituent. Examples of the substituent include a halogen atom (e.g., fluorine, chlorine atoms), a straight-chain, branched or cyclic, and saturated or unsaturated alkyl group having from 1 to 32 carbon atom(s) (e.g., methyl, ethyl, propyl, isopropyl, butyl, t-butyl, t-amyl, cyclopentyl, cyclohexyl, octyl, 2-ethylhexyl, and dodecyl groups), an aryl group having from 6 to 20 carbon atoms (e.g., phenyl, naphthyl, and anthryl groups), an acyloxy group having from 1 to 32 carbon atom(s) (e.g., acetoxy, tetradecanoyloxy, and benzoyloxy groups), a carbamoyloxy group having from 1 to 32 carbon atoms (e.g., a N,N-dimethylcarbamoyloxy group), an acylamino group having from 1 to 32 carbon atom(s) (e.g., acetamido, hexanoylamino, and benzoylamino groups), a sulfonamido group having from 1 to 32 carbon atom(s) (e.g., methanesulfonamido, dodecanesulfonamido, benzenesulfonamido, and p-toluenesulfonamido groups), a carbamoyl group having from 1 to 32 carbon atom(s) (e.g., N-methylcarbamoyl, N,N-diethylcarbamoyl, and N-octylcarbamoyl groups), a sulfamoyl group having from 0 to 32 carbon atom(s) (e.g., N-butylsulfamoyl, and N,N-diethylsulfamoyl groups), an alkoxy group having from 1 to 32 carbon atom(s) (e.g., methoxy, propoxy, isopropoxy, octyloxy, t-octyloxy, and dodecyloxy groups), an aryloxy group having from 7 to 32 carbon atoms (e.g., phenoxy, 4-methoxyphenoxy, and naphthoxy groups), an aryloxycarbonyl group having from 7 to 32 carbon atoms (e.g., phenoxycarbonyl, and naphthoxycarbonyl groups), an alkoxycarbonyl group having from 2 to 32 carbon atoms (e.g., methoxycarbonyl, and t-butoxycarbonyl groups), a N-acylsulfamoyl group having from 1 to 32 carbon atom(s) (e.g., N-tetradecanoylsulfamoyl, and N-benzoylcarbonyl groups), an alkylsulfonyl group having from 1 to 32 carbon atom(s) (e.g., methanesulfonyl, and octanesulfonyl groups), an arylsulfonyl group having from 6 to 32 carbon atoms (e.g., benzenesulfonyl, and p-toluenesulfonyl groups), an alkoxycarbonylamino group having from 2 to 32 carbon atoms (e.g., an ethoxycarbonylamino group), an aryloxycarbonylamino group having from 7 to 32 carbon atoms (e.g., phenoxycarbonylamino, and naphthoxycarbonylamino groups), an amino group having from 0 to 32 carbon atom(s) (e.g., amino, methylamino, diethylamino, diisopropylamino, and anilino groups), a cyano group, a nitro group, a carboxy group, a hydroxy group, a sulfo group, a mercapto group, an alkylthio group having from 1 to 32 carbon atom(s) (e.g., methylthio, and octylthio groups), an arylthio group having from 6 to 32 carbon atoms (e.g., phenylthio, and naphthylthio groups), an ureido group having from 1 to 32 carbon atom(s) (e.g., 3-methylureido, 3,3-dimethylureido, and 1,3-diphenylureido groups), a heterocyclic group having from 2 to 32 carbon atoms (e.g., 3- to 12-membered single ring or condensed ring containing at least one hetero atom such as nitrogen, oxygen and sulfur atoms, for example, 2-furyl, 2-pyranyl, 2-thienyl, 2-pyridyl, 2-imidazolyl, 4-morpholyl and 2-quinolyl groups), an acyl group having from 1 to 32 carbon atoms (e.g., acetyl and benzoyl groups), and a sulfamoylamino group having from 1 to 32 carbon atom(s) (e.g., N-butylsulfamoylamino and N-phenylsulfamoylamino groups). Of these substituents, the substituent that can be further substituted, may have another substituent such as an organic connecting group that connects with a carbon atom, an oxygen atom, a nitrogen atom, or a sulfur atom, and a halogen atom.

$R_3$ represents an alkyl group (e.g., a straight-chain or branched alkyl group, an aralkyl group, an alkenyl group, an alkynyl groups, a cycloalkyl group, or a cycloalkenyl group, having from 1 to 32 carbon atom(s)), an aryl group, a heterocyclic ring group (the heterocyclic ring is, for example, a 5- or 6-membered saturated or unsaturated heterocyclic ring containing at least one hetero atom selected from an oxygen atom, a nitrogen atom and a sulfur atom. The kind and number of the hetero atom that constitutes the ring may be one or more, respectively), —$OR_4$, or —$NR_5R_6$, which may be substituted with a substituent. Examples of the substituent are the same as those described with respect to $R_1$ and $R_2$.

$R_4$, $R_5$ and $R_6$ each represent an alkyl group (e.g., a straight-chain, or branched alkyl group, an aralkyl group, an alkenyl group, an alkynyl group, a cycloalkyl group, a cycloalkenyl group, having from 1 to 32 atom(s)), an aryl group, or a heterocyclic ring group (the heterocyclic ring is, for example, a 5- or 6-membered saturated or unsaturated heterocyclic ring containing at least one hetero atom selected from an oxygen atom, a nitrogen atom and a sulfur atom. The kind and number of the hetero atom that constitute the ring may be one or more, respectively), with the proviso that $R_6$ may be a hydrogen atom. These groups may be substituted with a substituent, and examples of the substituents are the same as those described with respect to $R_1$ and $R_2$.

X represents a hydrogen atom, an acyl group, or a sulfonyl group. The acyl group and the sulfonyl group may be substituted with a substituent, respectively. Examples of the substituent are the same as those described with respect to $R_1$ and $R_2$.

Z represent two or more non-metal atoms necessary to complete a 5- or 6-membered heterocyclic nucleus, or a condensed ring including a 5- or 6-membered heterocyclic nucleus. The heterocyclic ring and the condensed ring including a heterocyclic ring nucleus may be substituted with a substituent, respectively. Examples of the substituent are the same as those for $R_1$ and $R_2$ as described above.

Preferred examples of $R_1$ and $R_2$ include an alkyl group (e.g., a straight-chain or branched alkyl group, an aralkyl group, an alkenyl group, an alkynyl group, a cycloalkyl group, or a cycloalkenyl group) that is unsubstituted or substituted with one or more substituents selected from the group consisting of a halogen atom, a hydroxy group, an alkoxy group, a carboxy group and a sulfo group, and that has from 1 to 20 carbon atom(s); and an aryl group that is unsubstituted or substituted with one or more substituents selected from the group consisting of a halogen atom, a hydroxy group, an alkoxy group, a carboxy group and a sulfo group, and that has from 6 to 20 carbon atoms.

Still more preferred examples of $R_1$ and $R_2$ include an alkyl group (e.g., a straight-chain or branched alkyl group, an aralkyl group, an alkenyl group, an alkynyl group, a cycloalkyl group, a cycloalkenyl group) that is unsubstituted or substituted with one or more substituents selected from a halogen atom, a hydroxy group, an alkoxy group, a carboxy group, and a sulfo group, and that has from 1 to 10 carbon atom(s).

Most preferred examples of $R_1$ and $R_2$ include methyl, ethyl, n-propyl, isopropyl, n-butyl, isobutyl, n-pentyl, cyclohexyl, benzyl, 2,2,2-trifluoroethyl, 1,1,2,2-tetrafluoroethyl, 2,2,3,3-tetrafluoro-n-propyl, 1,1,1,3,3,3-hexafluoroisopropyl, pentafluorobenzyl, 2-hydroxyethyl, 3-hydroxybutyl, 2,3-dihydroxypropyl, hydroxyethoxyethyl, 2-carboxyethyl, 3-carboxy-n-propyl, 4-carboxy-n-butyl, methoxyethyl, methoxyethoxyethyl, 2-sulfoethyl, 3-sulfo-n-propyl, and 4-sulfo-n-butyl groups.

Preferred examples of $R_3$ include an alkyl group (e.g., a straight-chain or branched alkyl group, an aralkyl group, an alkenyl group, an alkynyl group, a cycloalkyl group, a cycloalkenyl group) that is unsubstituted or substituted with one or more substituents, and that has from 1 to 32 carbon atoms; an aryl group that is unsubstituted or substituted with one or more substituents, and that has from 6 to 10 carbon atoms; —$OR_4$, and —$NR_5R_6$.

Examples of the preferable substituent for $R_3$ include a halogen atom, a hydroxy group, a carboxy group, a sulfo group, a straight-chain, branched or cyclic, and saturated or unsaturated alkyl group having from 1 to 20 carbon atom(s) (e.g., methyl, ethyl, propyl, butyl, t-butyl, t-amyl, cyclopentyl, cyclohexyl, octyl, 2-ethylhexyl, dodecyl, and octadecyl groups), an aryl group having from 6 to 20 carbon atoms (e.g., phenyl and naphthyl groups), an acylamino groups having from 1 to 20 carbon atom(s) (e.g., acetamido, hexanoylamino, tetradecanoylamino, benzoylamino, and 4-dodecyloxybenzoylamino groups), a sulfonamido group having from 1 to 20 carbon atom(s) (e.g., methanesulfonamido, dodecanesulfonamido, benzenesulfonamido, p-toluenesulfonamido, and p-dodecyloxysulfonamido groups), a carbamoyl group having from 1 to 20 carbon atom(s) (e.g., N-methylcarbamoyl, N-dodecylcarbamoyl, N-phenylcarbamoyl, and N,N-diphenylcarbamoyl groups), an alkoxy group having from 1 to 20 carbon atoms (e.g., methoxy, propyloxy, isopropyloxy, t-octyloxy, and dodecyloxy groups), an aryloxy group having from 6 to 20 carbon atoms (e.g., phenoxy, and 4-methoxyphenoxy groups), an aryloxycarbonyl group having from 7 to 20 carbon atoms (e.g., phenoxycarbonyl, 4-methoxyphenoxy groups), an alkoxycarbonyl group having from 2 to 20 carbon atoms (e.g., methoxycarbonyl group, t-butoxycarbonyl, and tetradecyloxycarbonyl groups), an aryloxycarbonylamino group having from 7 to 20 carbon atoms (e.g., phenoxycarbonylamino, and naphthylcarbonylamino groups), an alkoxycarbonylamino group having from 2 to 20 carbon atoms (e.g., ethoxycarbonylamino, and dodecyloxycarbonylamino groups), and an ureido group having from 1 to 20 carbon atom(s) (e.g., 3-methylureido, 3-dodecylureido, 3-phenylureido, and 3,3-diphenylureido groups).

Still more preferred examples of $R_3$ include methyl, hexyl, hexadecyl, octadecyl, cyclohexyl, phenyl, 4-dodecyloxyphenyl, 3-octyloxycarbonylphenyl, 2,4-dimethoxy-5-tetradecylphenyl, 4-chlorophenyl, 2,5-dichlorophenyl, 3,5-dimethoxycarbonylphenyl, 3,5-dioctyloxycarbonylphenyl, 3-carboxyphenyl, 2-hydroxymethylphenyl, —$OR_4$ and —$NR_5R_6$ groups. Of these groups, the —$NR_5R_6$ group is most preferred.

Preferred examples of $R_4$, $R_5$ and $R_6$ include an alkyl group (e.g., a straight-chain or branched alkyl group, an aralkyl group, an alkenyl group, an alkynyl group, a cycloalkyl group, a cycloalkenyl group) that is unsubstituted or substituted with one or more substituents and that has from 1 to 32 carbon atom(s); and an aryl group that is unsubstituted or substituted with one or more substituents and that has from 6 to 10 carbon atoms. $R_6$ can be a hydrogen atom, preferably.

Preferred examples of the substituent for $R_4$, $R_5$ and $R_6$ include a halogen atom, a hydroxy group, a carboxy group, a sulfo group, a straight-chain, branched, or cyclic, and saturated or unsaturated alkyl group having from 1 to 20 carbon atoms (e.g., methyl, ethyl, propyl, butyl, t-butyl, t-amyl, cyclopentyl, cyclohexyl, octyl, 2-ethylhexyl, dodecyl, and octadecyl groups), an aryl group having from 6 to 20 carbon atoms (e.g., phenyl and naphthyl groups), an acylamino group having from 1 to 20 carbon atom(s) (e.g., acetamido, hexanoylamino, tetradecanoylamino, benzoylamino, and 4-dodecyloxybenzoylamino groups), a sulfonamido group having from 1 to 20 carbon atom(s) (e.g., methanesulfonamido, dodecanesulfonamido, benzenesulfonamido, p-toluenesulfonamido, and p-dodecyloxysulfonamido groups), a carbamoyl group having from 1 to 20 carbon atom(s) (e.g., N-methylcarbamoyl, N-dodecylcarbamoyl, N-phenylcarbamoyl, and N,N-diphenylcarbamoyl groups), an alkoxy group having from 1 to 20 carbon atom(s) (e.g., methoxy, propyloxy, isopropyloxy, t-octyloxy, and dodecyloxy groups), an aryloxy group having from 6 to 20 carbon atoms (e.g., phenoxy, and 4-methoxyphenoxy groups), an aryloxycarbonyl group having from 7 to 20 carbon atoms (e.g., phenyloxycarbonyl, and 4-methoxyphenoxycarbonyl groups), an alkoxycarbonyl group having from 2 to 20 carbon atoms (e.g., methoxycarbonyl, t-butoxycarbonyl, and tetradecyloxycarbonyl groups), an aryloxycarbonylamino group having from 7 to 20 carbon atoms (e.g., phenoxycarbonylamino, and naphthoxycarbonylamino groups), an alkoxycarbonylamino group having from 2 to 20 carbon atoms (e.g., ethoxycarbonylamino, and dodecyloxycarbonylamino groups), and an ureido group having from 1 to 20 carbon atom(s) (e.g., 3-methylureido, 3-dodecylureido, 3-phenylureido, and 3,3-diphenylureido groups).

Still more preferred examples of $R_4$ and $R_5$ include methyl, hexyl, hexadecyl, octadecyl, cyclohexyl, phenyl, 4-dodecyloxyphenyl, 3-octyloxycarbonylphenyl, 2,4-dimethoxy-5-tetradecylphenyl, 4-chlorophenyl, 2,5-dichlorophenyl, 3,5-dimethoxycarbonylphenyl, 3,5-dioctyloxycarbonylphenyl, and 3-carboxyphenyl groups.

Still more preferred examples of $R_6$ include a hydrogen atom, and methyl, hexyl, hexadecyl, octadecyl, cyclohexyl, phenyl, 4-dodecyloxyphenyl, 3-octyloxycarbonylphenyl, 2,4-dimethoxy-5-tetradecylphenyl, 4-chlorophenyl, 2,5-dichlorophenyl, 3,5-dimethoxycarbonylphenyl, 3,5-dioctyloxycarbonylphenyl, and 3-carboxyphenyl groups. Of these groups, a hydrogen atom is most preferred.

Preferred examples of X include a hydrogen atom, an acyl group having from 2 to 10 carbon atoms (e.g., acetyl and hexanoyl groups), an alkylsulfonyl group having from 1 to 10 carbon atom(s) (e.g., methanesulfonyl, and ethanesulfonyl groups), and an arylsulfonyl group having from 6 to 10 carbon atoms (e.g., benzenesulfonyl, and p-toluenesulfonyl groups). These groups may be unsubstituted or substituted with one or more substituents. Preferred examples of the substituent include a halogen atom, and hydroxy, alkoxy, carboxy, and sulfo groups.

More preferred examples of X include a hydrogen atom, an acyl group that is unsubstituted or substituted with a halogen atom, a hydroxy group, an alkoxy group, a carboxy group or a sulfo group and that has from 2 to 5 carbon atoms; an alkylsulfonyl group having from 1 to 4 carbon atom(s), and a benzenesulfonyl group.

Still more preferred examples of X include a hydrogen atom, and acetyl, propanoyl, chloroacetyl, benzoyl, 4-chlorobenzoyl, 2,4,6-trichlorobenzoyl, methanesulfonyl, ethanesulfonyl, trifluoromethanesulfonyl, benzenesulfonyl, 4-chlorobenzenesulfonyl, 2,5-dichlorobenzenesulfonyl, and pentafluorobenzenesulfonyl groups. Of these groups, a hydrogen atom is most preferred.

Z preferably represents non-metal atoms necessary to complete an imidazole nucleus, a benzimidazole nucleus, an ethyleneurea nucleus, or a tetrahydropyrimidone nucleus, each of which hetero ring may be unsubstituted or substituted with a substituent. Preferred examples of the substituent include a halogen atom, a hydroxy group, an alkoxy group, a carboxy group, a sulfo group, and an alkoxy group or an alkyl group that is unsubstituted or substituted with one or more substituents selected from a halogen atom, a hydroxy group, an alkoxy group, a carboxy group, and a sulfo group.

When the hydrazone compound represented by general formula (A) corresponds to a carbonyl compound, and $R_1$ and $R_2$ each represent a hydrogen atom, still more preferred examples of the heterocyclic ring completed by Z include 2-imidazolone, 4-chloro-2-imidazolone, 4,5-dichloro-2-imidazolone, 2-benzimidazolone, 5-chloro-2-benzimidazolone, 5,6-dichloro-2-benzimidazolone, ethyleneurea, 4-methylethyleneurea, 4,5-dimethylethyleneurea, and tetrahydropyrimidone.

Specific examples of typical developing agents represented by general formula (A) according to the present invention are illustrated below, but the present invention is not restricted to them.

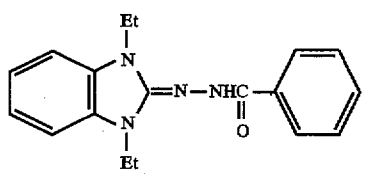

A-1

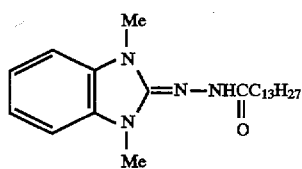

A-2

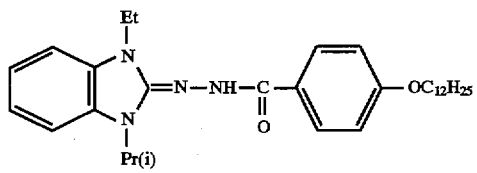

A-3

-continued
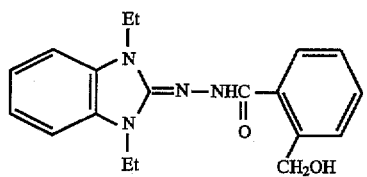
A-4
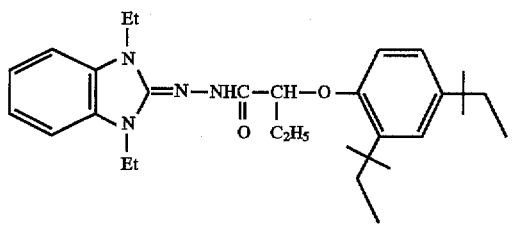
A-5
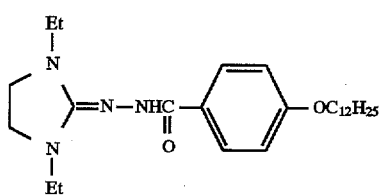
A-6
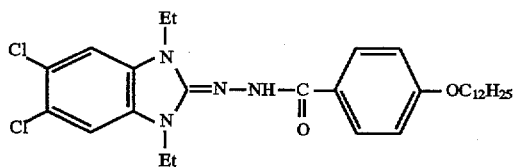
A-7
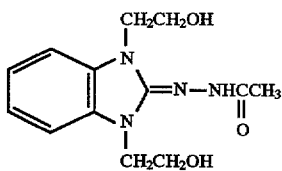
A-8
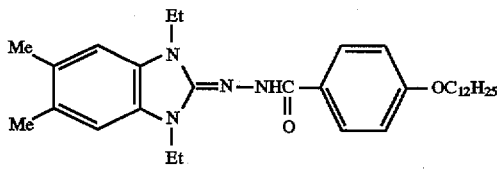
A-9
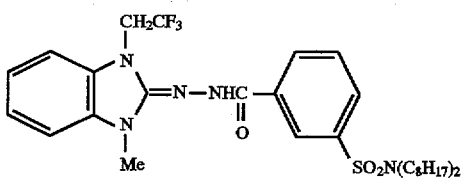
A-10
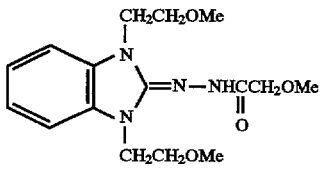
A-11
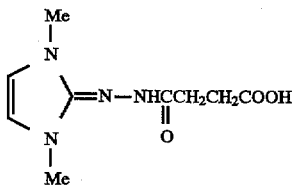
A-12

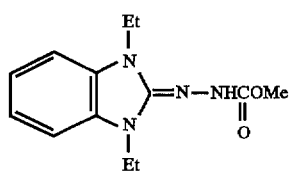 A-13
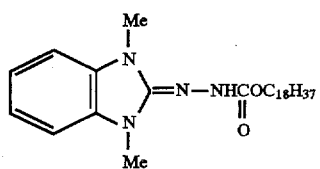 A-14
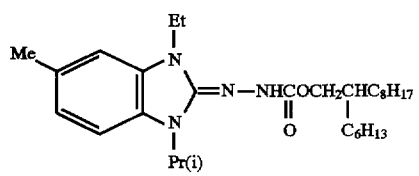 A-15
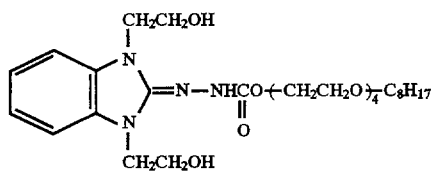 A-16
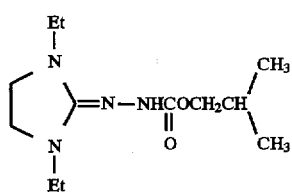 A-17
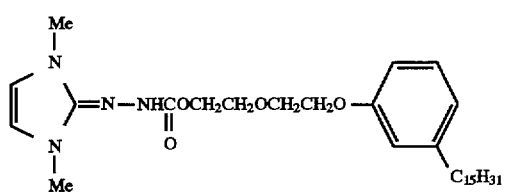 A-18
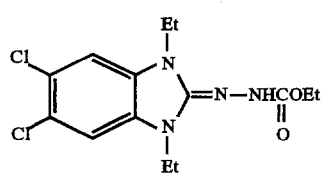 A-19
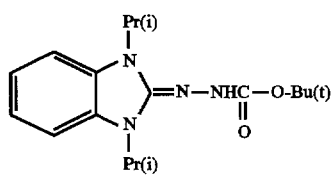 A-20
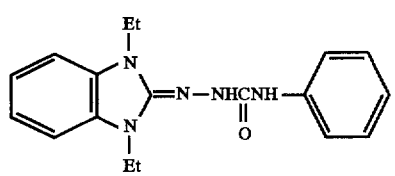 A-21

-continued
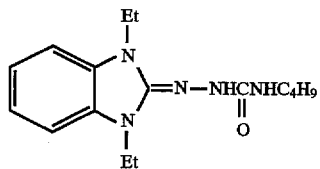
A-22
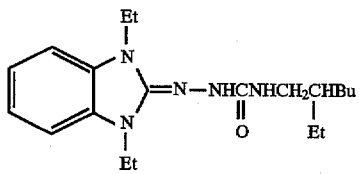
A-23
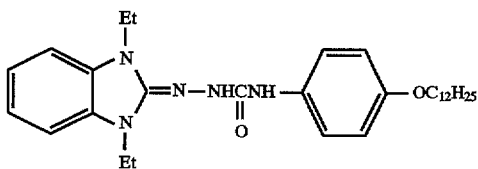
A-24
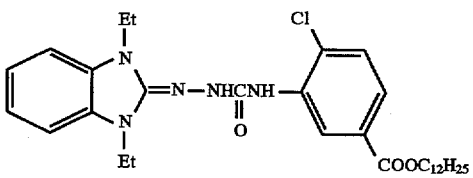
A-25
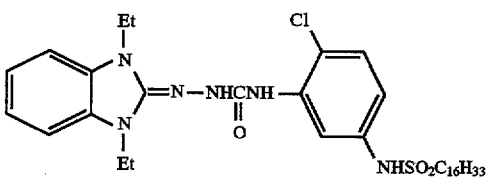
A-26
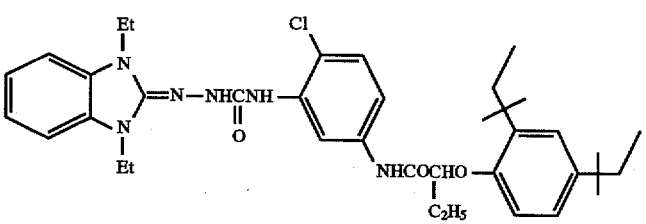
A-27
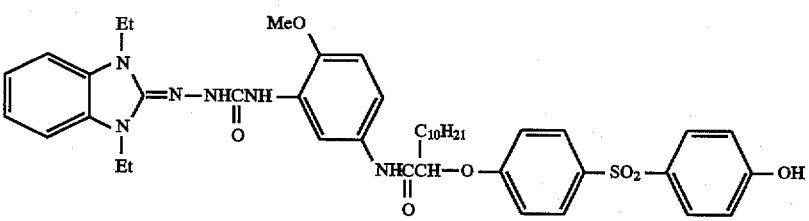
A-28
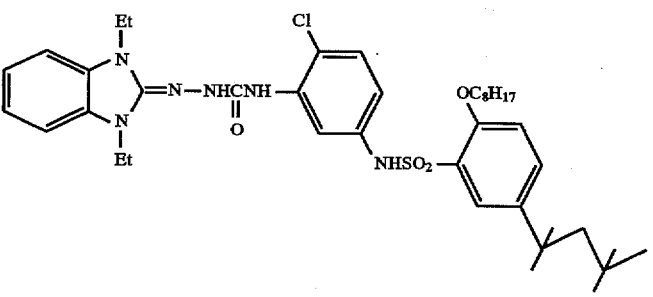
A-29

-continued
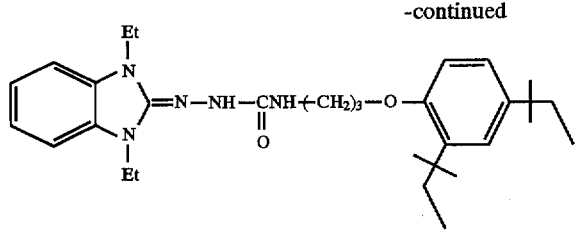
A-30
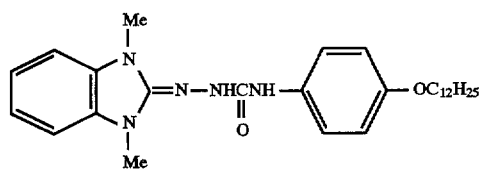
A-31
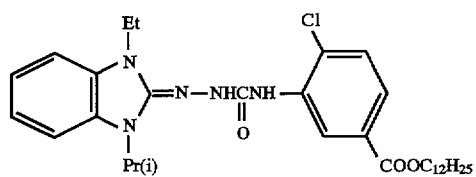
A-32
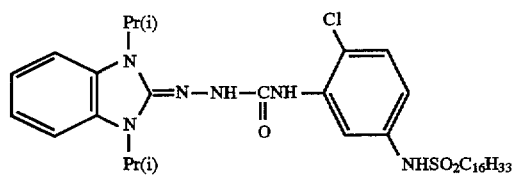
A-33
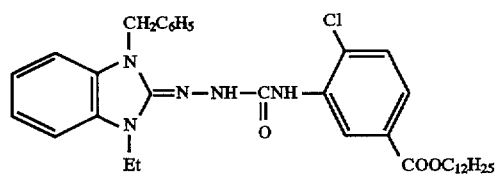
A-34
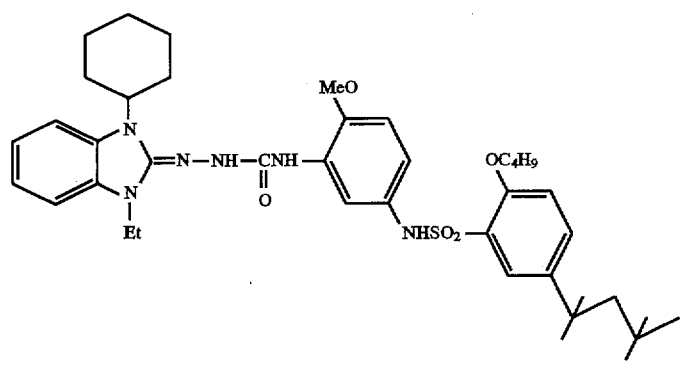
A-35
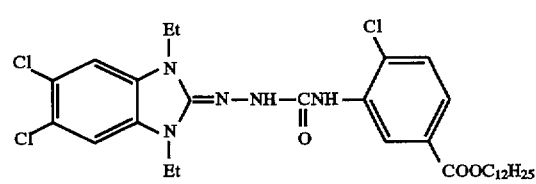
A-36
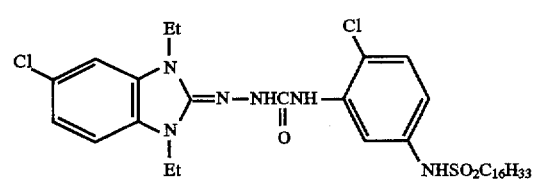
A-37

-continued
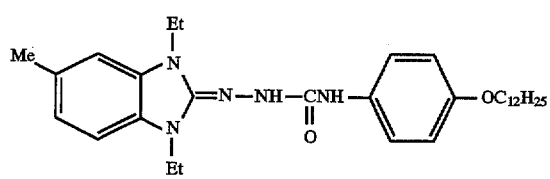
A-38
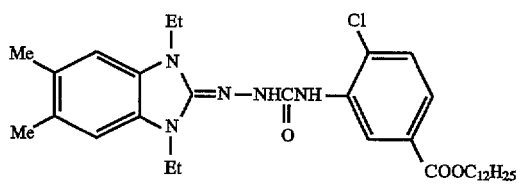
A-39
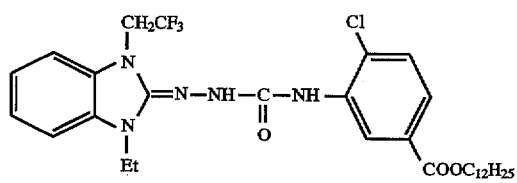
A-40
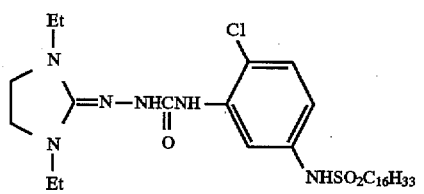
A-41
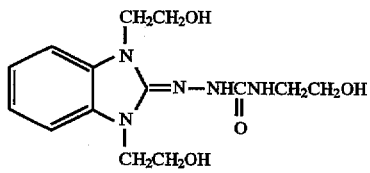
A-42
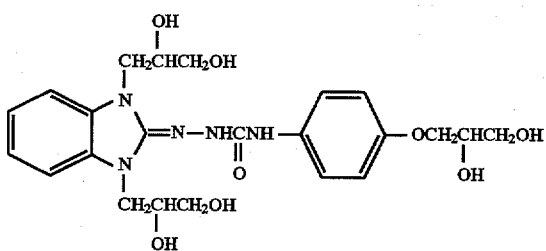
A-43
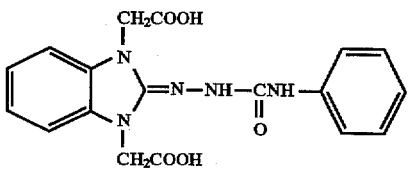
A-44
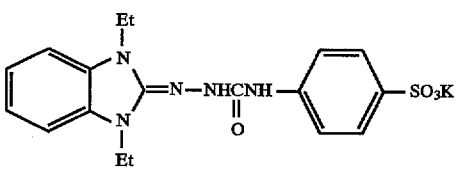
A-45

-continued

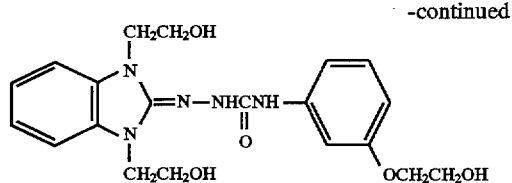
A-46

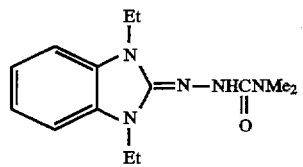
A-47

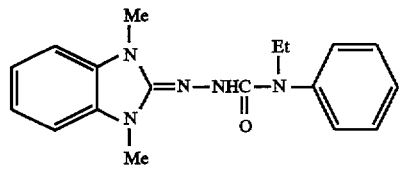
A-48

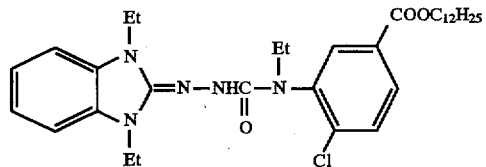
A-49

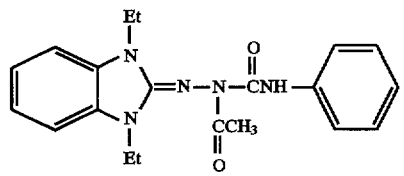
A-50

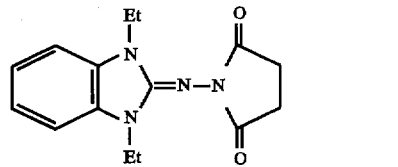
A-51

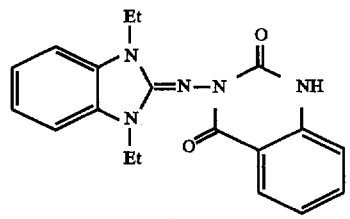
A-52

Color-developing agents according to the present invention can be prepared according to the method described, for example, in *Leibig Annalen der Chemie*, Vol. 609, p. 169 (1957). Further, they are prepared according to the following synthesis examples or in similar ways.

Synthesis Example 1

The exemplified compound (A-1) according to the present invention was synthesized according to the schema illustrated below.

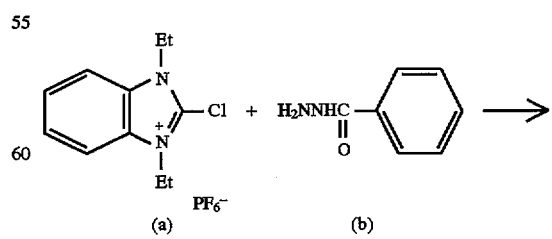

-continued

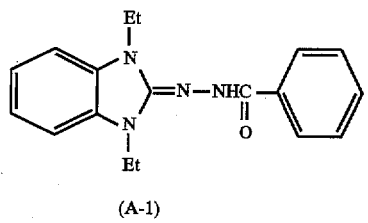

(A-1)

Synthesis of Exemplified compound (A-1)

To 80 ml of ethanol, were added 18 g of (a) and 6.9 g of (b), and the mixture was refluxed by heat for 3 hours, with stirring. The reaction mixture, after it had cooled to room temperature, was poured into an about-2N aqueous ammonia solution, and then the reaction product was extracted with ethyl acetate. The thus extracted solution was washed with brine, dried, and concentrated. The residue was recrystallized from a mixture of ethyl acetate and hexane, to obtain 7.2 g of the compound (A-1). Its chemical structure was identified by each spectrum of NMR, IR, and MS.

Synthesis Example 2

The exemplified compound (A-25) according to the present invention was synthesized according to the schema illustrated below.

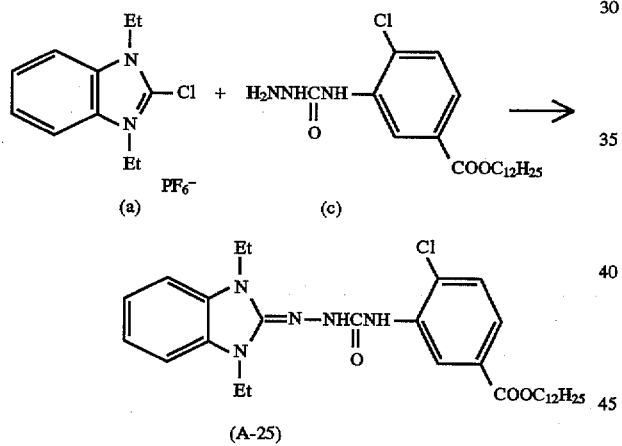

Synthesis of Exemplified compound (A-25)

To 80 ml of ethanol, were added 7.1 g of (a) and 8.0 g of (c), and the mixture was refluxed by heat for 4 hours with stirring. The reaction mixture, after it had cooled to room temperature, was poured into an about-2N aqueous ammonia solution, and then the reaction product was extracted with ethyl acetate. The thus extracted solution was washed with brine, dried, and concentrated. The residue was recrystallized from methanol, to obtain 8.5 g of the compound (A-25). Its chemical structure was identified by each spectrum of NMR, IR, and MS.

Other exemplified compounds were prepared in the similar manner as in the methods as described above.

The compound according to the present invention can be used for all silver halide light-sensitive material, such as color nega films, color papers, color reversal films and papers, and light-sensitive materials for X ray and graphic art, in which a dye image is used.

Further, the developing agent according to the present invention can be added to a silver halide light-sensitive material, and/or a processing composition (e.g. a processing solution).

A silver halide light-sensitive material in which the compound of the present invention is incorporated can be developed by heat processing or activator processing.

The heat processing for a light-sensitive material is known in the field of this technology, and the heat-developing light-sensitive material and its processing are described in, for example, *Fundamentals of Photographic Technology* (Shashin kogaku no Kiso), published by Corona Co., pp. 553–555 (1979); *Reflection Information* (Eizo Joho) (April 1978), page 40; Nebletts Handbook of Photography and Reprography 7th Ed. (Van Nostrand Reinhold Company), pp. 32–33; U.S. Pat. Nos. 3,152,904, 3,301,678, 3,392,020, and 3,457,075; British Patent Nos. 1,131,108, and 1,167,777; and *Research Disclosure* (RD-17029), pp. 9–15 (June 1978).

The terminology "activator processing" means a processing method that comprises developing a light-sensitive material incorporating a developing agent (color-developing agent) therein, with a processing solution that does not contain (free from) any developing agent. The above-mentioned processing solution does not contain a developing agent that is contained in an ordinary developing solution (components), but it may contain other components (e.g. alkali, a supplemental developing agent). The activator processing is described in such publications as EP 545, 491A1 and 565,165A1.

When the compound according to the present invention is used for a color photographic light-sensitive material, at least three silver halide emulsion layers, each of which has a spectral sensitivity in a different spectral region from the others, are used in combination, in order to obtain a wide range of color on a chromaticity diagram, by the use of three primary colors of yellow, magenta, and cyan. For example, there are a combination of a blue-sensitive layer, a green-sensitive layer, and a red-sensitive layer, and a combination of a green-sensitive layer, a red-sensitive layer, and an infrared-sensitive layer. Each of the light-sensitive layers may be set according to various configuration orders that are known for ordinary color photographic light-sensitive materials. Further, each of these light-sensitive layers may be divided into two or more layers, if necessary.

In the light-sensitive material, various supplemental layers, such as a protective layer, a subbing layer, an interlayer, an antihalation layer, and a back layer, may be set. Further, various kinds of filter dyes may be added to a photographic constituent layer, in order to improve color separation.

When the color-developing agent of the present invention is incorporated in a light-sensitive material, the amount of the color-developing agent to be added generally depends on the kind of a silver halide, and also on the kind of additives to be added according to the occasion, but it is preferably from 0.01 mol to 20 mol, and most preferably from 0.1 to 10 mol, per mol of silver.

The color-developing agent of the present invention may be added in any layers of the light-sensitive material, as long as the layer is suitable for the color-developing agent to initiate a desired reaction at the time of processing. That is to say, the color-developing agent must be placed at a position where a coupler and the color-developing agent of the present invention are able to form a useful dye image upon suitable processing in the presence of a light-sensitive silver halide and an electron-transferring agent after imagewise exposure to light.

Generally, the color-developing agent of the present invention is used with a dye-providing compound. In the present invention, the dye-providing compound is generally incorporated in a light-sensitive material, and a compound that is capable of forming a dye by an oxidation coupling reaction, i.e. a coupler, is used as the dye-providing compound. The coupler may be a 4-equivalent coupler or a 2-equivalent coupler, but 2-equivalent couplers are preferred in the present invention. Specific examples of the 4-equivalent and 2-equivalent couplers are fully described, for example, in Theory of The Photographic Process, 4th Ed., edited by T. H. James, published by Macmillan, pp. 291-334 and 354-361 (1977); and in JP-A Nos. 12353/1983, 149046/1983, 149047/1983, 11114/1984, 124399/1984, 174835/1984, 231539/1984, 231540/1984, 2951/1985, 14242/1985, 23474/1985, and 66249/1985.

The color-developing agent according to the present invention can be contained in, instead of a photographic material, a processing solution, such as a developer. In this case, preferably the amount to be added is 0.1 g to 100 g, and more preferably 1 g to 20 g, per liter.

Examples of couplers that are preferably used in the present invention are listed below:

As couplers that are preferably used in the present invention, compounds having structures described by the following formulae (1) to (12) are mentioned. They are compounds collectively generally referred to as active methylenes, pyrazolones, pyrazoloazoles, phenols, naphthols, and pyrrolotriazoles, respectively, which are compounds known in the art.

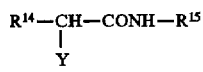 (1)

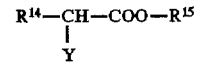 (2)

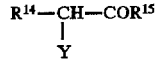 (3)

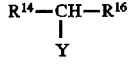 (4)

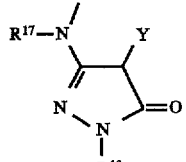 (5)

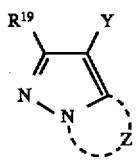 (6)

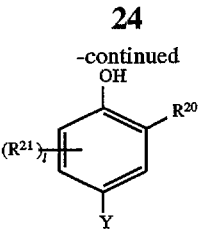 (7)

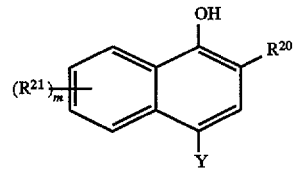 (8)

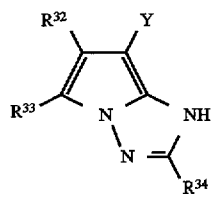 (9)

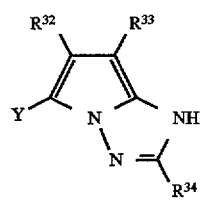 (10)

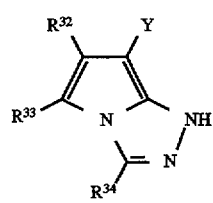 (11)

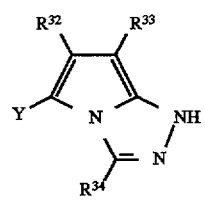 (12)

Formulae (1) to (4) represent couplers that are called active methylene couplers, and, in the formulae, $R^{14}$ represents an acyl group, a cyano group, a nitro group, an aryl group, a heterocyclic group, an alkoxycarbonyl group, an aryloxycarbonyl group, a carbamoyl group, a sulfamoyl group, an alkylsulfonyl group, or an arylsulfonyl group, optionally substituted.

In formulae (1) to (3), $R^{15}$ represents an optionally substituted alkyl group, aryl group, or heterocyclic group. In formula (4), $R^{16}$ represents an optionally substituted aryl group or heterocyclic group. Examples of the substituent that may be possessed by $R^{14}$, $R^{15}$, and $R^{16}$ include those mentioned for $R_1$ and $R_2$.

In formulae (1) to (4), Y represents a hydrogen atom or a group capable of coupling split-off by coupling reaction with the oxidized product of the developing agent. Examples of Y are a heterocyclic group (a saturated or unsaturated 5-membered to 7-membered monocyclic or condensed ring having as a hetero atom at least one nitrogen atom, oxygen atom, sulfur atom, or the like, e.g. succinimido, maleinimido, phthalimido, diglycolimido, pyrrole, pyrazole, imidazole, 1,2,4-triazole, tetrazole, indole, benzopyrazole, benzimidazole, benzotriazole, imidazolin-2,4-dione, oxazolidin-2,4-dione, thiazolidin-2,4-dione, imidazolidin-2-one, oxazolin-2-one, thiazolin-2-one, benzimidazolin-2-one, benzoxazolin-2-one, benzthiazolin-2-one, 2-pyrrolin-5-one, 2-imidazolin-5-one, indolin-2,3-dione, 2,6-dioxypurine, parabic acid, 1,2,4-triazolidin-3,5-dione, 2-pyridone, 4-pyridone, 2-pyrimidone, 6-pyridazone, 2-pyrazone, 2-amino-1,3,4-thiazolidine, and 2-imino-1,3,4-thiazolidin-4-one), a halogen atom (e.g. a chlorine atom and a bromine atom), an aryloxy group (e.g. phenoxy and 1-naphthoxy), a heterocyclic oxy group (e.g. pyridyloxy and pyrazolyoxy), an alkoxy group (e.g. methoxy and dodecyloxy), an acyloxy group (e.g. acetoxy and benzoyloxy), a carbamoyloxy group (e.g. N,N-diethylcarbamoyloxy and morpholinocarbonyloxy), an aryloxycarbonyloxy group (e.g. phenylcarbonyloxy), an alkoxycarbonyloxy group (e.g. methoxycarbonyloxy and ethoxycarbonyloxy), an arylthio group (e.g. phenylthio and naphthylthio), a heterocyclic thio group (e.g. tetrazolylthio, 1,3,4-thiadiazolylthio, 1,3,4-oxadiazolylthio, and benzimidazolylthio), an alkylthio group (e.g. methylthio, and dodecylthio), an alkylsulfonyloxy group (e.g. methanesulfonyloxy), an arylsulfonyloxy group (e.g. benzenesulfonyloxy and toluenesulfonyloxy), an amido group (e.g. acetamido and trifluoroacetylamido), a sulfonamido group (e.g. methanesulfonamido and benzenesulfonamido), an alkylsulfonyl group (e.g. methanesulfonyl), an arylsulfonyl group (e.g. benzenesulfonyl and toluenesulfonyl), an alkylsulfinyl group (e.g. methanesulfinyl), an arylsulfinyl group (e.g. benzenesulfinyl and toluenesulfinyl), an arylazo group (e.g. phenylazo and 4-methoxyphenylazo), and a carbamoylamino group (e.g. N-methylcarbamoylamino).

Y may be substituted, and examples of the substituent that may be possessed by Y include those mentioned for $R_1$ and $R_2$.

Preferably Y represents a halogen atom, an aryloxy group, a heterocyclic oxy group, an acyloxy group, an aryloxycarbonyloxy group, an alkoxycarbonyloxy group, or a carbamoyloxy group.

In formulae (1) to (4), $R^{14}$ and $R^{15}$, and $R^{14}$ and $R^{16}$, may bond together to form a ring.

Formula (5) represents a coupler that is called a 5-pyrazolone magenta coupler, and in the formula, $R^{17}$ represents an alkyl group, an aryl group, an acyl group, or a carbamoyl group. $R^{18}$ represents a phenyl group or a phenyl group that is substituted by one or more halogen atoms, alkyl groups, cyano groups, alkoxy groups, alkoxycarbonyl groups, or acylamino groups. Y has the same meaning as that in formulae(1) to (4).

Preferable 5-pyrazolone magenta couplers represented by formula (5) are those wherein $R^{17}$ represents an aryl group or an acyl group, and $R^{18}$ represents a phenyl group that is substituted by one or more halogen atoms.

With respect to these preferable groups, more particularly, $R^{17}$ is an aryl group, such as a phenyl group, a 2-chlorophenyl group, a 2-methoxyphenyl group, a 2-chloro-5-tetradecaneamidophenyl group, a 2-chloro-5-(3-octadecenyl-1-succinimido)phenyl group, a 2-chloro-5-octadecylsulfonamidophenyl group, and a 2-chloro-5-[2-(4-hydroxy-3-t-butylphenoxy)tetradecaneamido]phenyl group; or $R_{17}$ is an acyl group, such as an acetyl group, a pivaroyl group, a tetradecanoyl group, a 2-(2,4-di-t-pentylphenoxy) acetyl group, a 2-(2,4-di-t-pentylphenoxy)butanoyl group, a benzoyl group, and a 3-(2,4-di-t-amylphenoxyacetazido) benzoyl group, any of which may have a substituent, such as a halogen atom or an organic substituent that is bonded through a carbon atom, an oxygen atom, a nitrogen atom, or a sulfur atom.

Preferably $R^{18}$ represents a substituted phenyl group, such as a 2,4,6-trichlorophenyl group, a 2,5-dichlorophenyl group, and a 2-chlorophenyl group.

Preferred examples of Y are the same as those described for formulae (1) to (4).

Formula (6) represents a coupler that is called a pyrazoloazole coupler, and, in the formula, $R^{19}$ represents a hydrogen atom or a substituent. Z represents a group of nonmetal atoms required to form a 5-membered azole ring having 2 to 4 nitrogen atoms, which azole ring may have a substituent (including a condensed ring). Y has the same meaning as that in formulae (1) to (4).

Preferable pyrazoloazole couplers represented by formula (6), in view of spectral absorption characteristics of the color-formed dyes, are imidazo[1,2-b]pyrazoles described in U.S. Pat. No. 4,500,630, pyrazolo[1,5-b][1,2,4]triazoles described in U.S. Pat. No. 4,540,654, and pyrazolo[5,1-c][1,2,4]triazoles described in U.S. Pat. No. 3,725,067, with preference given to pyrazolo[1,5,-b][1,2,4]triazoles in view of fastness to light.

Details of substituents of the azole rings represented by the substituents $R^{19}$, Y and Z are described, for example, in U.S. Pat. No. 4,540,654, the second column, line 41, to the eighth column, line 27. Preferable pyrazoloazole couplers are pyrazoloazole couplers having a branched alkyl group directly bonded to the 2-, 3-, or 6-position of the pyrazolotriazole group, as described in JP-A No. 65245/1986; pyrazoloazole couplers containing a sulfonamido group in the molecule, as described in JP-A No. 65245/1986; pyrazoloazole couplers having an alkoxyphenylsulfonamido ballasting group, as described in JP-A No. 147254/1986; pyrazolotriazole couplers having an alkoxy group or an aryloxy group at the 6-position, as described in JP-A Nos. 209457/1987 or 307453/1988; and pyrazolotriazole couplers having a carbonamido group in the molecule, as described in Japanese Patent Application No. 22279/1989.

Preferred examples of Y are the same as those described for formulae (1) to (4).

Formulae (7) and (8) are respectively called phenol couplers and naphthol couplers, and in the formulae $R^{20}$ represents a hydrogen atom, a halogen atom, or a group selected from the group consisting of —$CONR^{22}R^{23}$, —$SO_2NR^{22}R^{23}$, —$NHCOR^{22}$, —$NHSO_2R^{22}$, —$NHCONR^{22}R^{23}$, and —$NHSO_2NR^{22}R^{23}$. $R^{22}$ and $R^{23}$ each represent a hydrogen atom or a substituent. In formulae (7) and (8), $R^{21}$ represents a substituent, 1 is an integer selected from 0 to 2, and m is an integer selected from 0 to 4. Y has the same meaning as that in formulae (1) and (4). The substituents of $R^{21}$ to $R^{23}$ include those mentioned above as examples of substituents for $R_1$ and $R_2$.

Preferable examples of the phenol couplers represented by formula (7) include 2-acylamino-5-alkylphenol couplers described, for example, in U.S. Pat. Nos. 2,369,929, 2,801,171, 2,772,162, 2,895,826, and 3,772,002.

Preferable examples of the naphthol couplers represented by formula (8) include 2-carbamoyl-1-naphthol couplers described, for example, in U.S. Pat. Nos. 2,474,293, 4,052,212, 4,146,396, 4,282,233, and 4,296,200.

Preferred examples of Y are the same as those described for formulae (1) to (4).

Formulas (9) to (12) are couplers called pyrrolotriazoles and $R^{32}$, $R^{33}$, and $R^{34}$ each represent a hydrogen atom or a substituent. Y has the same meaning as defined for formulae (1) to (4). Examples of the substituent of $R^{32}$, $R^{33}$, and $R^{34}$ include those mentioned for $R_1$ and $R_2$. Preferable examples of the pyrrolotriazole couplers represented by formulae (9) to (12) include those wherein at least one of $R^{32}$ and $R^{33}$ is an electron-attracting group, which specific couplers are described in European Patent Nos. 488,248A1, 491,197A1, and 545,300.

Preferred examples of Y are the same as those described for formulae (1) to (4).

Further, couplers having such structures as a fused-ring phenol, an imidazole, a pyrrole, a 3-hydroxypyridine, an active methylene or methine, a 5,5-fused-ring heterocyclic ring, and a 5,6-fused-ring heterocyclic ring, can be used.

As the fused-ring phenol couplers, those described, for example, in U.S. Pat. Nos. 4,327,173, 4,564,586, and 4,904,575 can be used.

As the imidazole couplers, thouse described, for example, in U.S. Pat. Nos. 4,818,672 and 5,051,347 can be used.

As the pyrrole couplers, those described, for example, in JP-A Nos. 188137/1992, 190347/1992 can be used.

As the 3-hydroxypyridine couplers, those described, for example, in JP-A No. 315736/1989 can be used.

As the active methylene and active methine couplers, those described, for example, in U.S. Pat. Nos. 5,104,783 and 5,162,196 can be used.

As the 5,5-fused-ring heterocyclic ring couplers, for example, pyrrolopyrazole couplers described in U.S. Pat. No. 5,164,289, and pyrroloimidazole couplers described in JP-A No. 174429/1992, can be used.

As the 5,6-fused ring heterocyclic ring couplers, for example, pyrazolopyrimidine couplers described in U.S. Pat. No. 4,950,585, pyrrolotriazine couplers described in JP-A No. 204730/1992, and couplers described in European Patent No. 556,700, can be used.

In the present invention, in addition to the above couplers, use can be made of couplers described, for example, in West Germany Patent Nos. 3,819,051A and 3,823,049, U.S. Pat. Nos. 4,840,883, 5,024,930, 5,051,347, and 4,481,268, European Patent Nos. 304,856A2, 329,036, 354,549A2, 374,781A2, 379,110A2, and 386,930A1, and JP-A Nos. 141055/1988, 32260/1989, 32261/1989, 297547/1990, 44340/1990, 110555/1990, 7938/1991, 160440/1991, 172839/1991, 172447/1992, 179949/1992, 182645/1992, 184437/1992, 188138/1992, 188139/1992, 194647/1992, 204532/1992, 204731/1992, and 204732/1992.

Specific examples of the couplers that can be used in the present invention are shown below, but, of course, the present invention is not limited to them:

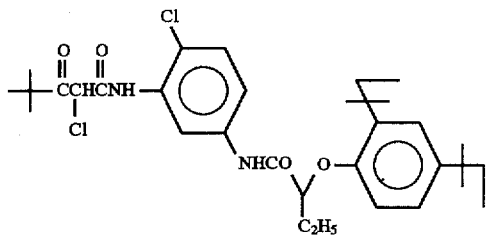

C-1

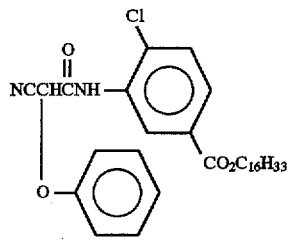

C-2

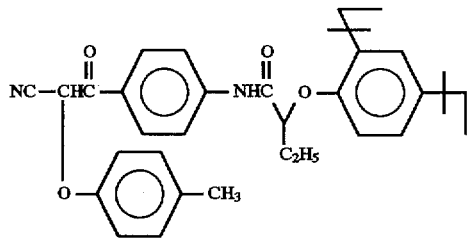

C-3

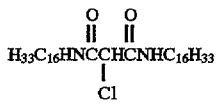

C-4

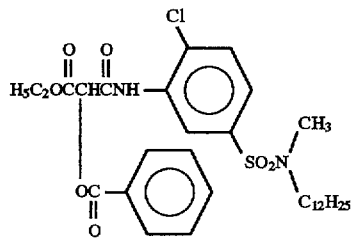

C-5

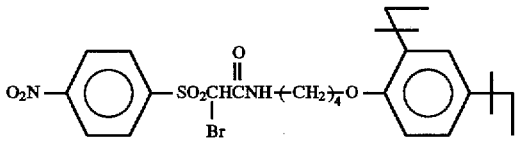

C-6

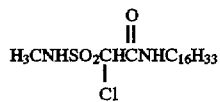

C-7

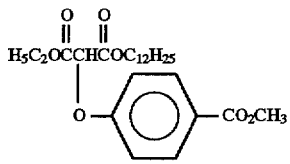

C-8

-continued
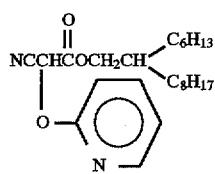 C-9
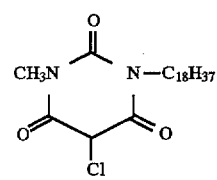 C-10
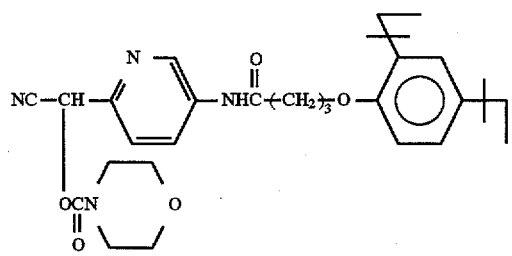 C-11
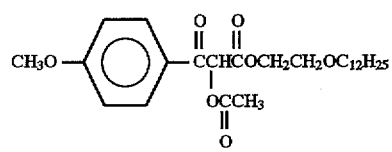 C-12
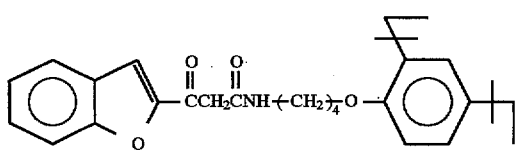 C-13
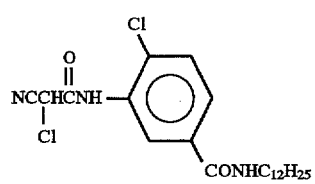 C-14
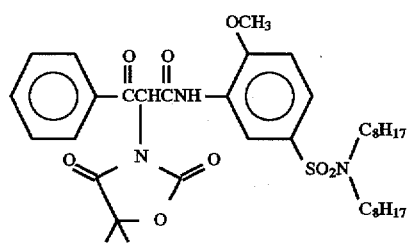 C-15
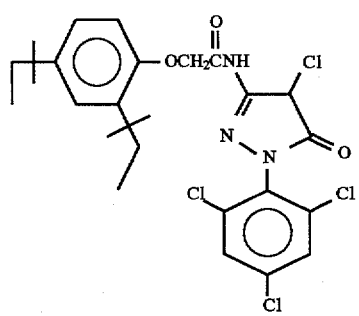 C-16
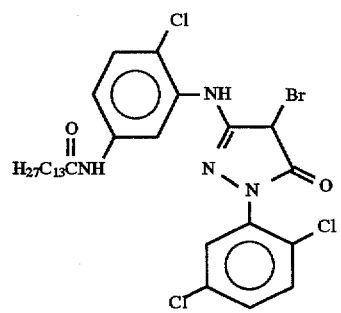 C-17
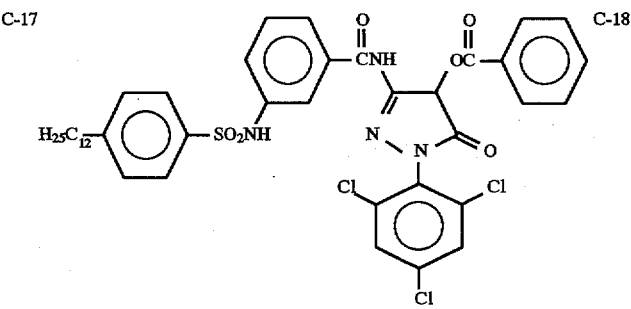 C-18
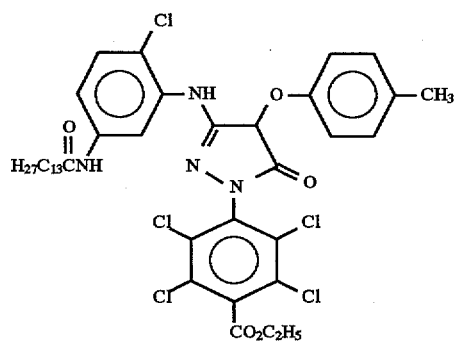 C-19
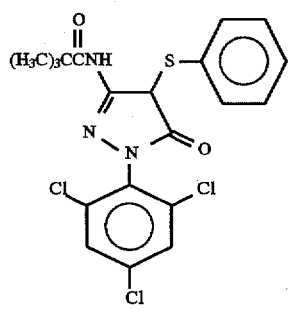 C-20

-continued
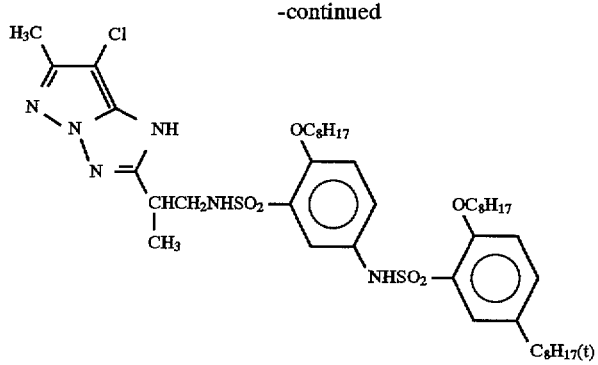
C-21
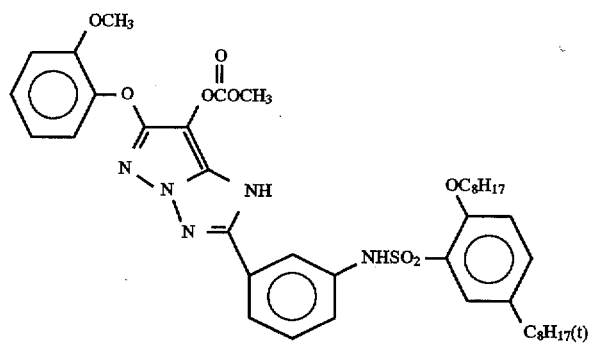
C-22
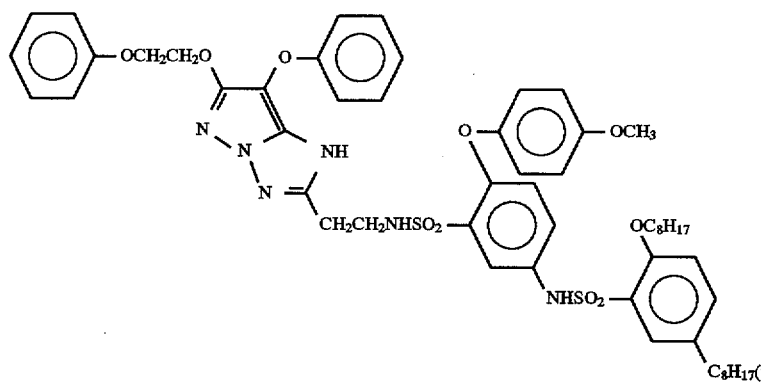
C-23
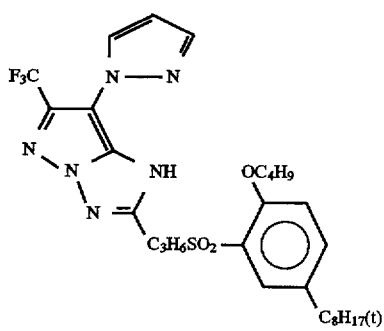
C-24
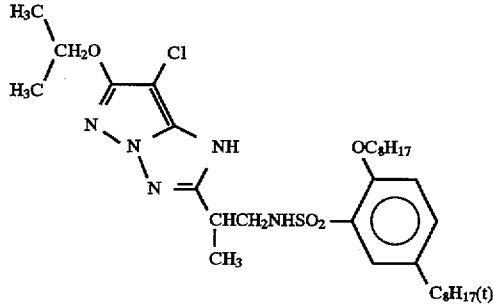
C-25
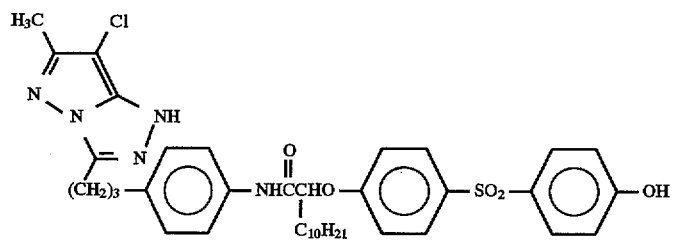
C-26

-continued
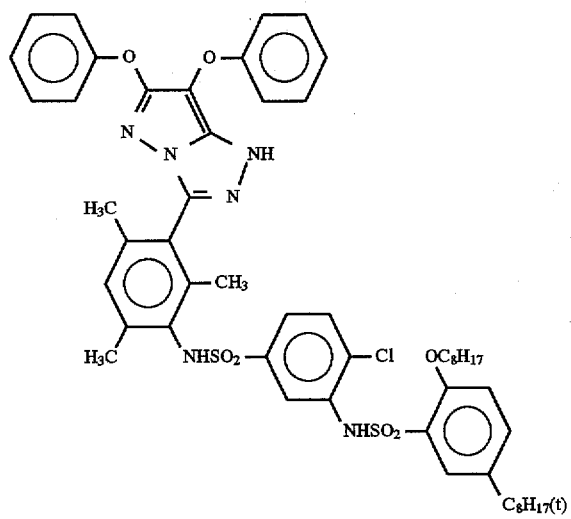
C-27
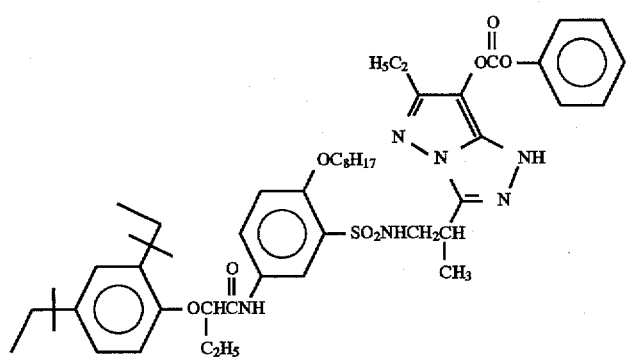
C-28
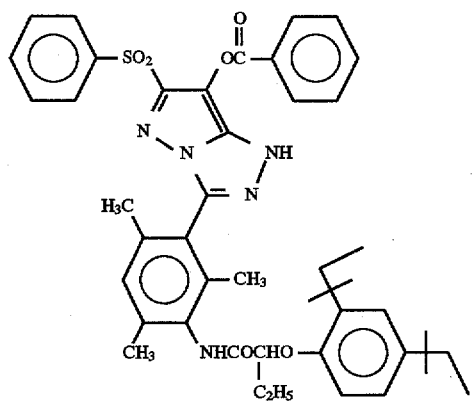
C-29
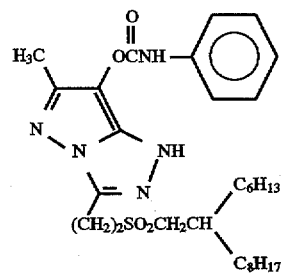
C-30
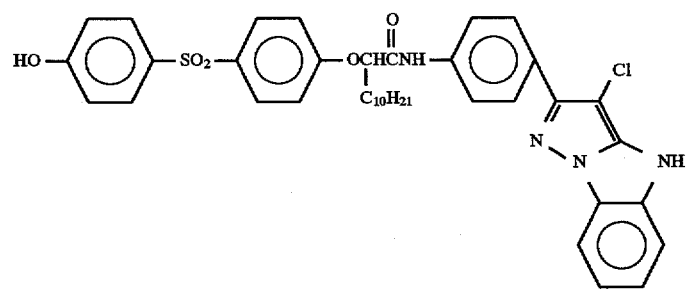
C-31

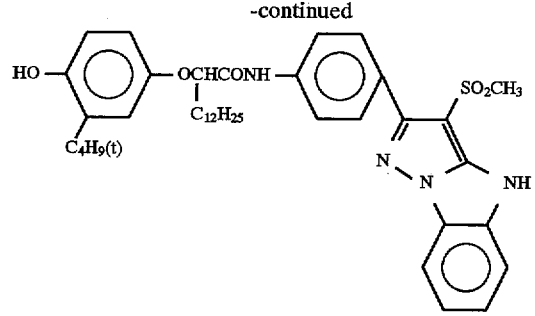
C-32
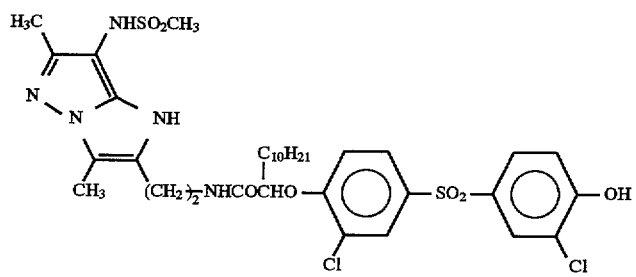
C-33
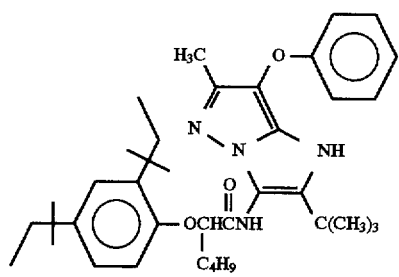
C-34
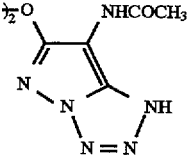
C-35
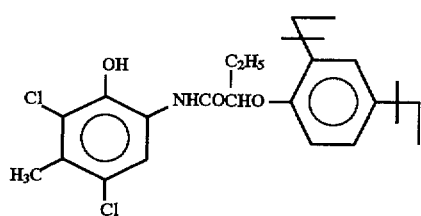
C-36
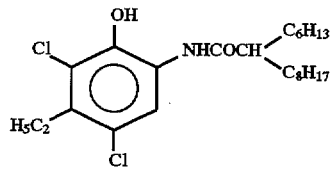
C-37
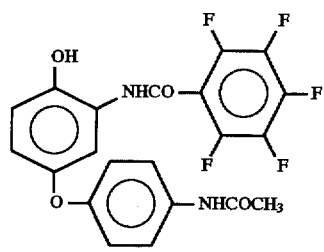
C-38
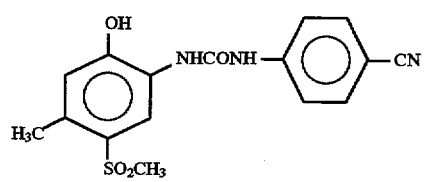
C-37
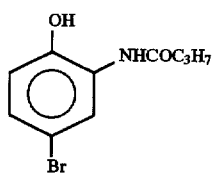
C-40
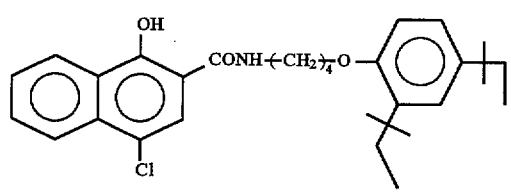
C-41

-continued
C-42
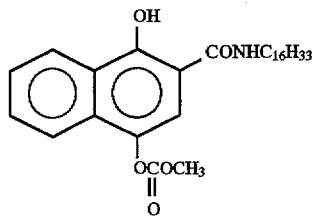
C-43
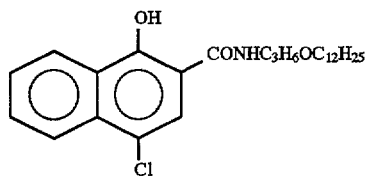
C-44
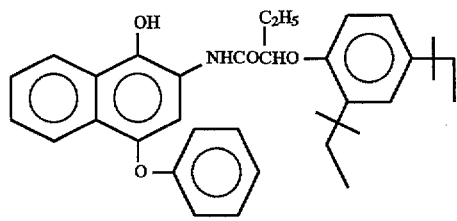
C-45
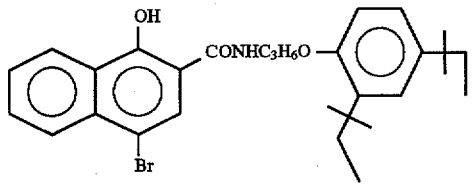
C-46
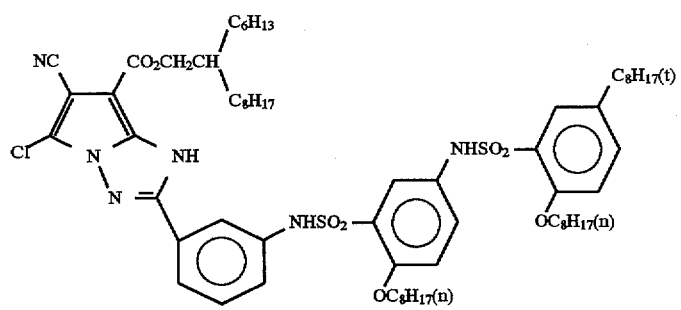
C-47
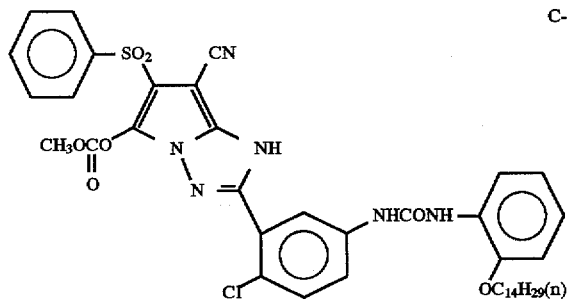
C-48
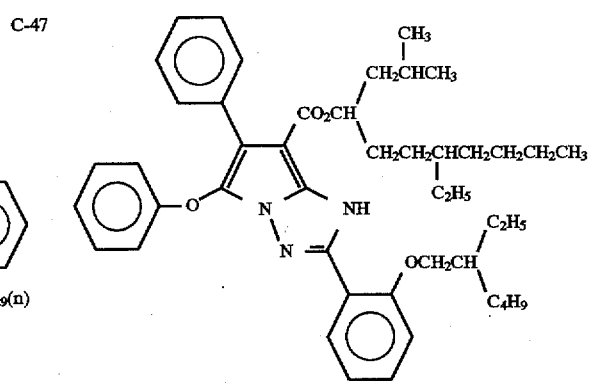
C-49
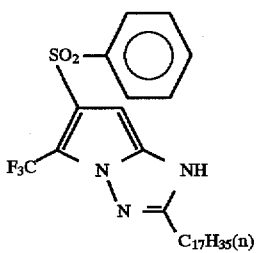
C-50
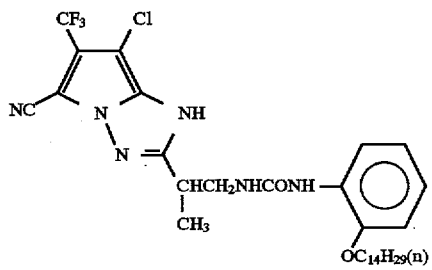

C-51
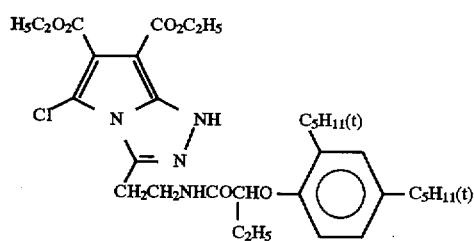
C-52
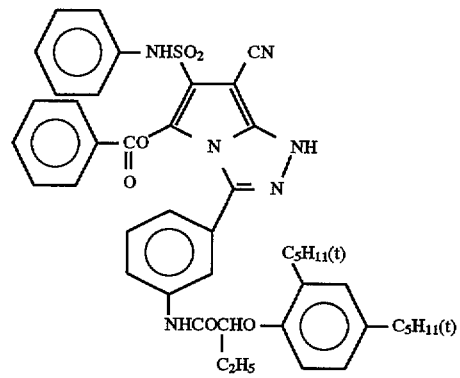
C-53
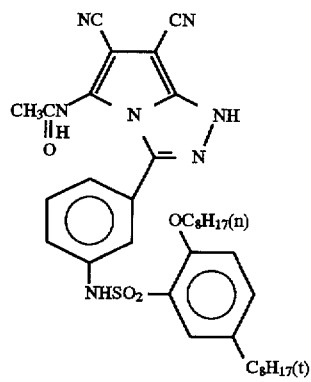
C-54
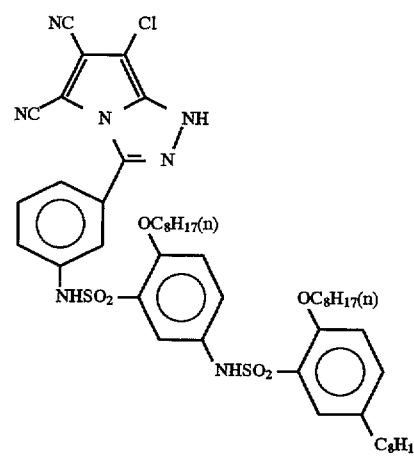
C-55
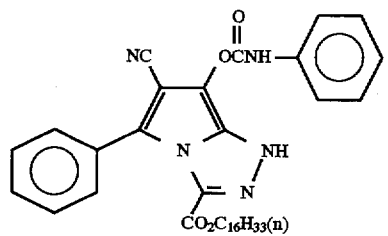
C-56
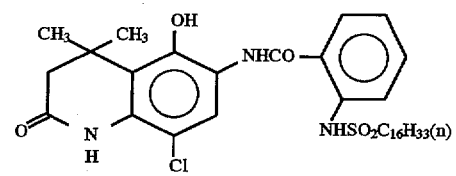
C-57
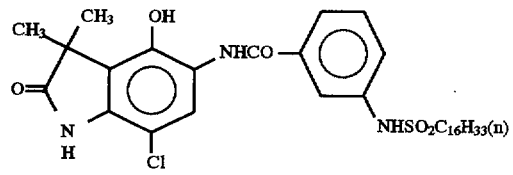
C-58
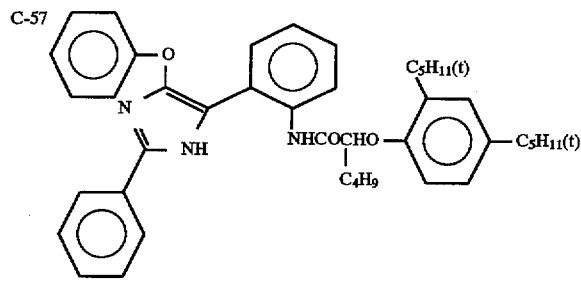
C-59
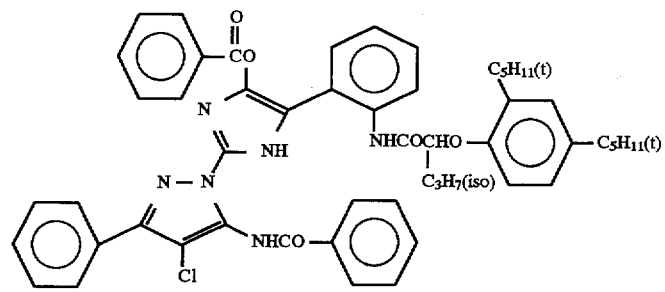

-continued
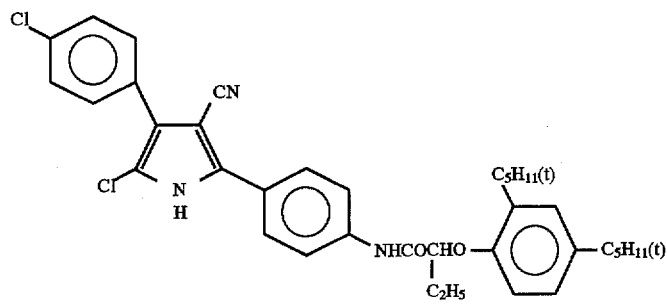
C-60
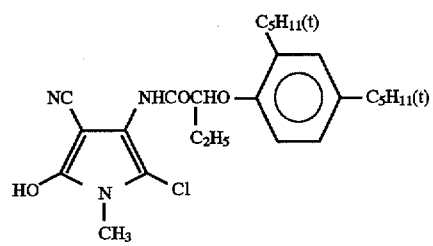
C-61
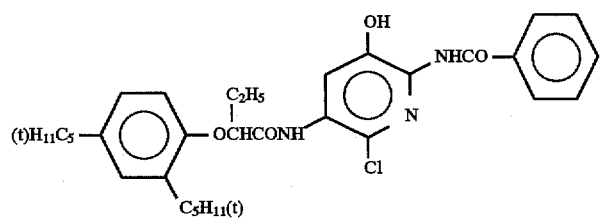
C-62
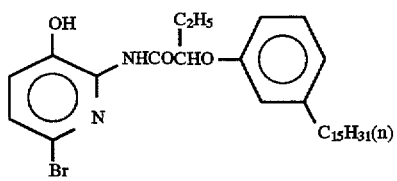
C-63
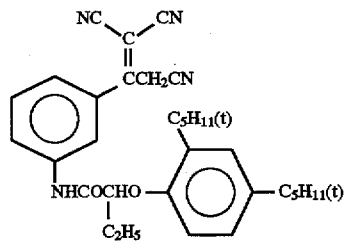
C-64
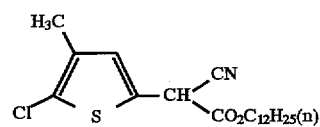
C-65
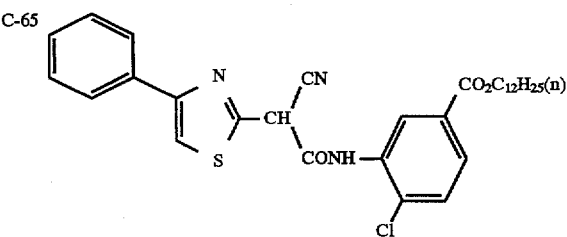
C-66
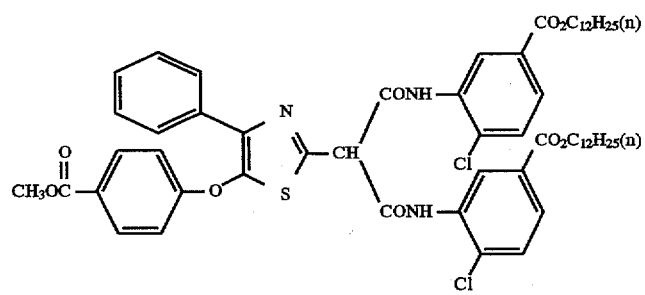
C-67

-continued
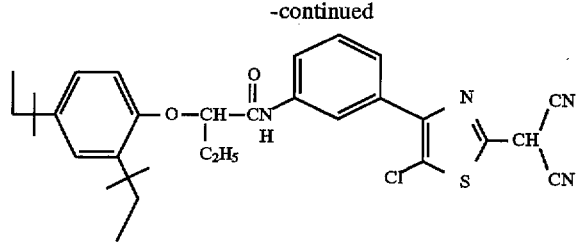 C-68
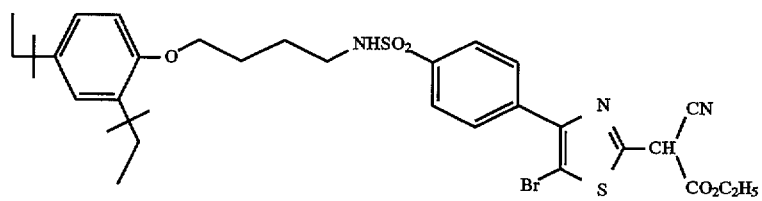 C-69
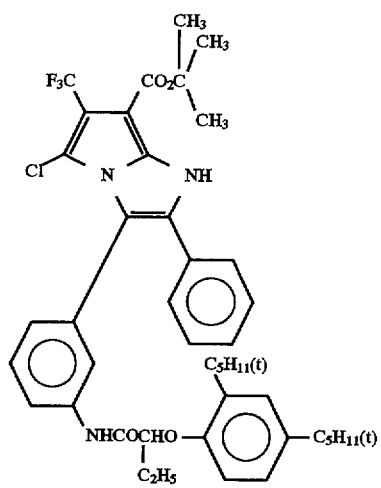 C-70
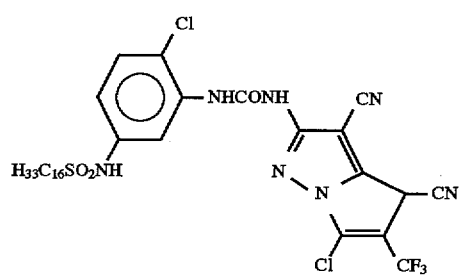 C-71
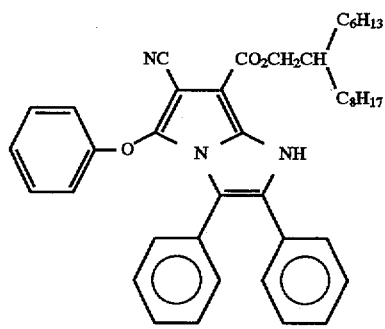 C-72
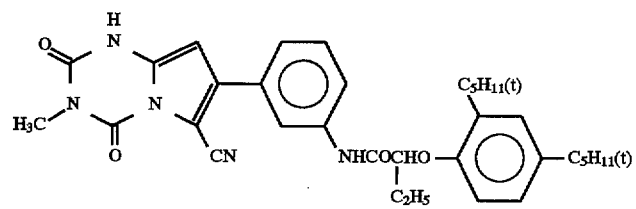 C-73

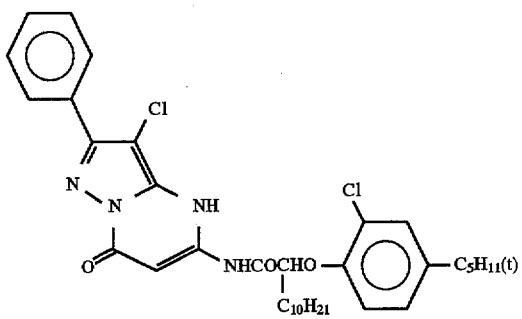

C-74

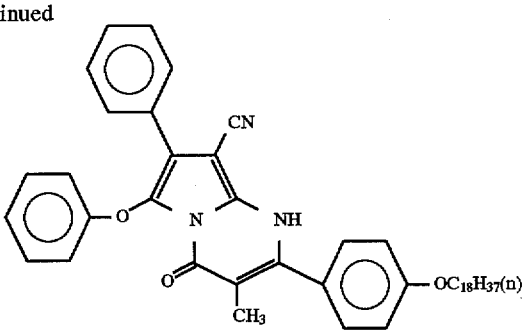

C-75

A light-sensitive material of the present invention fundamentally contains a light-sensitive silver halide, a coupler, as a dye-providing compound; a color-developing agent, and a binder, on a support. Further, the light-sensitive material may also contain an oxidizer of organic metal salts, etc., according to the occasion. In many cases, these ingredients are added into the same layer, but they may be added to separate layers, as long as they can react with each other.

The couplers and the color-developing agents for the use of the present invention may be incorporated in a light-sensitive material according to various known dispersion methods.

Examples of high-boiling-point solvents to be used in an oil-in-water dispersion method are described in U.S. Pat. No. 2,322,027. As examples of the high-boiling-point organic solvent having a boiling point of not lower than 175° C. at the atmosphere, which can be used in the oil-in-water dispersion method, there are mentioned phthalates (e.g., dibutyl phthalate, dicyclohexyl phthalate, di-2-ethylhexyl phthalate, decyl phthalate, bis(2,4-di-t-amylphenyl) phthalate, bis(2,4-di-t-amylphenyl) isophthalate, bis(1,1-di-ethylpropyl) phthalate, phosphates or phosphonates (e.g., triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, di-2-ethylhexylphenyl phosphonate), benzoates (e.g., 2-ethylhexyl benzoate, dodecyl benzoate, 2-ethylhexyl-p-hydroxybenzoate), amides (e.g., N,N-diethyldodecanamide, N,N-diethyllaurylamide, N-tetradecylpyrrolidone), alcohols or phenols (e.g., isostearyl alcohol, 2,4-di-tert-amylphenol), aliphatic carboxylic acid esters (e.g., bis(2-ethylhexyl) sebacate, dioctyl azelate, glycerol tributyrate, isostearyl lactate, trioctyl citrate), aniline derivatives (e.g., N,N-dibutyl-2-butoxy-5-tert-octylaniline), and hydrocarbons (e.g., paraffin, dodecylbenzene, diisopropylnaphthalene). As auxiliary solvents, there are mentioned, for example, organic solvents having a boiling point of approximately 30° C. or higher, preferably from 50° C. to about 160° C., with typical specific examples such as ethyl acetate, butyl acetate, ethyl propionate, methyl ethyl ketone, cyclohexanone, 2-ethoxyethyl acetate, and dimethylformamide.

The process of a latex dispersion method, the effect of the same, and specific examples of latexes for impregnation to be used in the method, are described in U.S. Pat. No. 4,199,363 and German Patent (OLS) Nos. 2,541,274 and 2,541,230.

The silver halide emulsion for use with the present invention may contain silver chloride, silver bromide, silver iodobromide, silver chlorobromide, silver chloroiodide, or silver chloroiodobromide.

The silver halide emulsion for use with the present invention may be a surface-latent-image-type emulsion or an internal-latent-image-type emulsion. The internal-latent-image-type emulsion can be used as a direct reversal emulsion in combination with a nucleating agent and/or a light-fogging agent. The silver halide emulsion may be a so-called core/shell-type emulsion having a different phase between the internal part and the surface layer of the silver halide grains. Further, silver halides of different composition may be fused on host silver halide grains by epitaxy. The silver halide emulsion may be monodispersed or polydispersed, but it is preferred to blend different kinds of monodispersed emulsions to regulate gradation, as disclosed in JP-A Nos. 167743/1989 and 223,463/1992. The grain size is preferably from 0.1 to 2 µm, and especially 0.2 to 1.5 µm. With respect to the form of the silver halide grains, a regular crystal form, such as a cubic form, an octahedral form, or a tetradecahedral form; an irregular crystal form, such as a sphere form or a tubular form having a high aspect ratio; or a form having crystal defects, such as a twin phase; or a composite of these forms, can be used.

The silver halide emulsion for use in the present invention can be prepared by processes described, for example, in U.S. Pat. Nos. 4,500,626, column 50, and 4,628,021; Research Disclosure (hereinafter abbreviated as RD) No. 17,029 (1978), ibid. No. 17,643, pp. 22–23 (Dec. 1978), ibid. No. 18,716, p. 648 (November 1979), ibid. No. 307,105, pp. 863–865 (Nov. 1989), JP-A Nos. 253159/1987, 13546/1989, 236546/1990, 110555/1991; by P. Glafkides in Chimie et Phisique Photographique (published by Paul Montel, 1967), by G. F. Duffin in Photographic Emulsion Chemistry (published by Focal Press, 1966), and by V. L. Zelikman et al. in Making and Coating Photographic Emulsion (published by Focal Press, 1964).

In the course of the preparation of the light-sensitive silver halide emulsion for use in the present invention, it is preferred to conduct so-called "desalting", to remove extra salts. As a method of the desalting, a noodle washing, in which gelatin is gelled, may be used. An alternative method is a sedimentation method, in which inorganic salts comprising a multivalence anion (e.g. sodium sulfate), anionic surfactants, anionic polymers (e.g. sodium salt of polystyrenesulfonic acid), or gelatin derivatives (e.g. gelatins modified with an aliphatic acyl group, an aromatic acyl group, or an aromatic carbamoyl group) can be used. The sedimentation method is preferably used.

The light-sensitive silver halide emulsion for use in the present invention may contain heavy metals, such as iridium, rhodium, platinum, cadmium, zinc, thallium, lead, iron, osmium, and chromium, according to purposes. The compounds comprising these metals can be used singly or in combination. Further, the metal compound can be added as a salt, such as a chloride, a bromide, and a cyanide, or as various complex salts. The amount of the metal compound to be added varies depending on the purpose of the use, but generally it is approximately from $10^{-9}$ to $10^{-3}$ mol per mol of silver halide. Further, the metal compound can be incorporated in the silver halide grains uniformly, or locally (i.e. in an interior part or a surface of grains). Specifically, a silver halide emulsion described, for example, in JP-A Nos. 236542/1990, 116637/1989, and Japanese Patent Application No. 126629/1992 can be preferably used.

At the time of the formation of silver halide grains in a light-sensitive silver halide emulsion for use in the present invention, thiocyanate salts, ammonia, thioether compounds in which four hydrogen atoms are substituted, organic thioether derivatives as described in JP-B No. 11386/1972, a sulfur-containing compound as described in JP-A No. 144319/1978, etc., can be used as a silver halide solvent.

Other conditions of the preparation can be found by referring such publications as the above described P. Glafkides, *Chimie et Phisique Photographique* (published by Paul Montel, 1967), G. F. Duffin, *Photographic Emulsion Chemistry* (published by Focal Press, 1966), and V. L. Zelikman et al., *Making and Coating Photographic Emulsion* (published by Focal Press, 1964). That is, any of the acid process, the neutral process, the ammonia process, and the like can be used, and as a method to react a soluble silver salt with a soluble halide, any of the single-jet method, the double-jet method, a combination of these methods, and the like can be used. The double-jet method preferably can be used to obtain a monodispersed emulsion.

A method wherein grains are formed in an atmosphere of excess silver ions (the so-called reverse precipitation method) can be also used. As one type of the double-jet method, a method wherein the pAg in the liquid phase, wherein the silver halide will be formed, is kept constant; that is, the so-called controlled double-jet method, can be used.

Further, in order to facilitate growth of the silver halide grains, the density of the silver salt and the halide to be added, an amount thereof, and an addition speed, can be increased, as described in, for example, JP-A-142,329/1980, JP-A-158124/1980, and U.S. Pat. No. 3,650,757.

Further, an agitation method of the reaction solution may be any of known agitation methods. Further, the temperature and the pH of the reaction liquid at the time of the formation of silver halide grains can be determined according to its object without any specific restrictions, but, a preferred pH range is from 2.2 to 8.5, and more preferably 2.5 to 7.5.

Generally the light-sensitive silver halide emulsion is chemically sensitized. With respect to the chemical sensitization for the light-sensitive silver halide emulsion that is used in the present invention, a chemical sensitization known for a conventional silver halide emulsion, such as a chalcogen sensitization, including sulfur sensitization, selenium sensitization, and tellurium sensitization; a noble metal sensitization that uses gold, platinum or palladium, and a reduction sensitization, can be used, alone or in combination, as described in, for example, JP-A No. 110555/1991 and Japanese Patent Application No. 75798/1992. These chemical sensitizations can be conducted in the presence of a nitrogen-containing heterocyclic compound, as described in JP-A-253159/1987. Further, the antifoggant hereinafter described can be added after the chemical sensitization. Specifically, the methods described in JP-A-45833/1993 and JP-A-40446/1987 can be used.

The pH at the time of chemical sensitization is preferably from 5.3 to 10.5, and more preferably from 5.5 to 8.5; and the pAg is from 6.0 to 10.5, and more preferably from 6.8 to 9.0.

The coating amount of the light-sensitive silver halide emulsion for use in the present invention is generally from 1 mg/m$^2$ to 10 g/m$^2$ in terms of silver.

For the purpose of spectrally sensitizing light-sensitive silver halide grains for use in the present invention to a wavelength region of green, red, or infrared, methine dyes and the like can be used. Further, if necessary, a blue-sensitive emulsion can be spectrally sensitized to a wavelength region of blue.

The dyes to be used include a cyanine dye, a merocyanine dye, a complex cyanine dye, a complex merocyanine dye, a horopolar cyanine dye, a hemicyanine dye, a styryl dye, and a hemioxonol dye.

Specific examples of the sensitizing dyes are described in U.S. Pat. No. 4,617,257, JP-A Nos. 180550/1984, 13546/1989, 45828/1993, and 45834/1993.

These sensitizing dyes can be used alone or in combination. The combination of dyes is often used especially for the purpose of super sensitization or adjustment of the wavelength of the spectral sensitivity.

A dye that does not itself have a function of spectral sensitization, or a compound that substantially does not absorb a visible light but that provides super sensitization, may be incorporated in a silver halide emulsion with a spectral sensitizing dye. Examples of these dyes and compounds are described in U.S. Pat. No. 3,615,641 and JP-A No. 23145/1988.

The time at which the sensitizing dye is added to the silver halide emulsion may be before or during the chemical ripening, or thereafter. Alternatively, the time may be before or after the formation of nuclei of silver halide grains, as described in U.S. Pat. Nos. 4,183,756 and 4,225,666. Further, these sensitizing dyes and supersensitizers may be added to the emulsion in the form of a solution of organic solvent, such as methanol; a dispersion of a hydrophilic colloid, such as gelatin; or a solution of a surfactant. The amount of these spectral sensitizing dyes to be added is generally in the range of approximately $10^{-8}$ mol to $10^{-2}$ mol, per mol of the silver halide.

Known photographic additives that can be used in the present invention are described in Research Disclosure, Nos. 17643, 18716, and 30710, as shown in the Table below.

| Additive | RD 17643 | RD 18716 | RD 307105 |
|---|---|---|---|
| 1. Chemical Sensitizer | p. 23 | p. 648, right column | p. 866 |
| 2. Sensitivity Increasing Agent | | p. 648, right column | |
| 3. Spectral Sensitizer, Super-sensitizer | pp. 23-24 | p. 648, right column to p. 649, right column | pp. 866-868 |
| 4. Brightening Agent | p. 24 | p. 647, right column | p. 868 |
| 5. Antifoggant, Stabilizer | pp. 24-25 | p. 649, right column | pp. 868-870 |
| 6. Light Absorber, Filter Dye, Ultraviolet ray Absorber | pp. 25-26 | p. 649, right column to p. 650, left column | p. 873 |
| 7. Antistain Agent | p. 25, right column | p. 650, left column to right column | p. 872 |

| Additive | RD 17643 | RD 18716 | RD 307105 |
| --- | --- | --- | --- |
| 8. Dye Image Stabilizer | p. 25 | p. 650, left column | p. 872 |
| 9. Hardening Agent | p. 26 | p. 651, left column | p. 874–875 |
| 10. Binder | p. 26 | p. 651, left column | pp. 873–874 |
| 11. Plasticizer, Lubricant | p. 27 | p. 650, right column | p. 876 |
| 12. Coating Aid, Surface Active Agent | pp. 26–27 | p. 650, right column | pp. 875–876 |
| 13. Antistatic Agent | p. 27 | p. 650, right column | pp. 876–877 |
| 14. Matting Agent | | | pp. 878–879 |

The light-sensitive material of the present invention preferably contains various additives for the purpose of preventing propagation of various fungi and bacteria, such as phenethyl alcohol; and 1,2-benzisothiazoline-3-on, n-butyl, p-hydroxybenzoate, phenol, 4-chloro-3,5-dimethylphenol, 2-phenoxyethanol, and 2-(4-thiazolyl)benzimidazole, as described in JP-A Nos. 257747/1988, 272248/1987, and 80941/1990.

Suitable supports for use in the present invention are described in, for example, the above-described RD No. 17643, p. 28; RD No. 18716, p. 647, right column, to p. 648, left column; and RD No. 307105, p. 879. Preferred examples of the support include a triacetate support (TAC) and a polyester support.

In the light-sensitive material of the present invention, the rate of swelling $T_{1/2}$ of all the hydrophilic colloidal layers on the side of the emulsion layers is preferably not more than 30 seconds, and more preferably not more than 20 seconds. The terminology "film thickness" as used herein means a film thickness as measured after conditions of 25° C. and 55% relative humidity for 2 days. The rate of swelling $T_{1/2}$ can be measured by a process known in the field of this technology; for example, by the use of a swellometer of the type described by A. Green et al. in *Photographic Science and Engineering*, vol. 19, No. 2, pp. 124–129. The terminology "rate of swelling $T_{1/2}$" means a time required for a light-sensitive material to be swollen to ½ the saturated swollen thickness; the saturated swollen thickness being defined as 90% of the maximum swollen thickness that is reached when the light-sensitive material is swollen with a color-developing solution at 30° C. for 3 minutes and 15 seconds.

The $T_{1/2}$ can be controlled by adding a proper amount of a hardening agent for a gelatin binder, or by varying aging conditions after coating.

The light-sensitive material of the present invention preferably contains, at the reverse side of the emulsion layer, a hydrophilic colloidal layer having a total dry thickness of 2 μm to 20 μm, which is called a back layer. The back layer preferably contains the above-described light absorber, a filter dye, an ultraviolet ray absorbing agent, an antistatic agent, a hardener, a binder, a plasticizer, a lubricant, a coating aid, a surface-active agent, and the like. The swelling rate of the back layer is preferably in the range of 2.5 to 6.0.

The silver halide photographic light-sensitive material of the present invention provides much more effects when applied to a film unit having a lens, as described, for example, in JP-B No. 32615/1990 and examined Japanese utility model Publication No. 39784/1991.

The compound according to the present invention is described below in detail with respect to its addition to a heat-developable silver halide light-sensitive material.

In the present invention, for the purpose of facilitating an electron transfer between the color-developing agent (i.e. the compound according to the present invention) and the developable silver halide, an electron-transferring agent and/or its precursor can be used in combination therewith, according to the occasion. Examples of the electron-transferring agent that can be used in the present invention are described in, for example, U.S. Pat. No. 4,500,626, columns 49–50; U.S. Pat. Nos. 4,839,272, 4,330,617, 4,590, 152, 5,017,454, and 5,139,919; JP-A No. 140335/1985, pp. 17–18; JP-A Nos. 40245/1982, 138736/1981, 178458/1984, 53831/1984, 182449/1984, 182450/1984, 119555/1985, 128436/1985, 128439/1985, 198540/1985, 181742/1985, 259253/1986, 201434/1987, 244044/1987, 131253/1987, 131256/1987, 10151/1988, 13546/1989, pp. 40–57; JP-A Nos. 120553/1989, 32338/1990, 35451/1990, 234158/1990, 160443/1991, and European Patent No. 220746, pp. 78–96. Preferred among the above-mentioned compounds are those described in the above-described U.S. Pat. No. 5,139,919, European Patent Publication No. 418,743, JP-A Nos. 138556/1990, and 102345/1992. Preferably used methods of stably introducing the electron-transferring agent into a layer are described in JP-A Nos. 230143/1990 and 235044/1990. Further, desirably the mobility of the electron-transferring agent or its precursor is greater than that of the diffusion-resistance-reducing agent (electron-donating agent). Especially useful electron-transferring agents are 1-phenyl-3-pyrazolidones, sulfonamidophenols, and aminophenols.

In the present invention, an oxidation product of the organic silver salt may be used with a light-sensitive silver halide emulsion. As an organic compound that can be used to form the oxidation product of the organic silver salt, benzotriazoles, aliphatic acids, and the like, as described in, for example, U.S. Pat. No. 4,500,626, columns 52–53, can be mentioned. Further, silver acetylene compounds are also useful, as described in U.S. Pat. No. 4,775,613. Two or more kinds of the organic silver salts may be used in combination.

The above-described organic silver salt generally can be used in an amount of 0.01 to 10 mol, preferably 0.01 to 1 mol, per mol of the light-sensitive silver halide. A total coating amount of the light-sensitive silver halide emulsion and the organic silver salt is generally in the range of 0.05 to 10 g/m², preferably 0.1 to 4 g/m², in terms of silver.

In the present invention, a base precursor may be incorporated in a light-sensitive material for the purposes of increasing sensitivity, reducing developing time, increasing image density, and improving stability. Preferred examples of the base precursor include compounds that are capable of releasing a base according to some heat reaction, such as salts of a base and an organic acid that is subjected to decarboxylic acid reaction by heat, and compounds that decomposes by a reaction such as an intramolecular nucleophilic substitution reaction, Lossen's rearrangement, and Beckmann's rearrangement to release amines; and compounds that generate a base by electrolysis or a complex-forming reaction. One base precursor of the type that releases a base by heat is a salt of trichloroacetic acid, as described in British Patent No. 998,959. Examples of the compounds having improved stability include a salt of α-sulfonylacetic acid, as described in U.S. Pat. No. 4,060, 420; a salt of propiol acetic acid, as described in Japanese Patent Application 55700/1983; 2-carboxycarboamide derivatives, as described in U.S. Pat. No. 4,088,496; a salt of a heat resoluble acid and an alkali metal or an alkali earth metal, in addition to an organic salt, as a base component (Japanese Patent Application 69597/1983); hydroxamic carbamates that are used Lossen's rearrangement, as described in Japanese Patent Application 43860/1983; and aldoxime-carbamates that form nitrile by heat, as described in Japanese Patent Application No. 31614/1983.

Moreover, base precursors, as described in, for example, British Patent Nos. 998,945 and 2,079,480, JP-A-226225/1980, U.S. Pat. Nos. 3,220,846, 4,514,493, and 4,657,848, and *Kochi Gijutsu*, No. 5 (published by Azutec L.R. Co., Mar. 22, 1991) p. 55, et seq., are also useful.

The heat developable light-sensitive image-recording material according to the present invention can be used to form a black/white image or a multicolor image. The image-recording material that is used to form a full-color image, generally has light-sensitive layers that each have a different spectral sensitivity, and that also each contain a compound that provides a dye having a different hue as a result of heat development.

Specifically, in order to obtain a wide range of color on a chromaticity diagram by the use of three primary colors, i.e. yellow, magenta, and cyan, at least three layers of silver halide emulsions, each of which is light-sensitive to a different spectral region, are used in combination. Examples of the combination include a combination of a blue-sensitive layer, a green-sensitive layer, and a red-sensitive layer; a combination of a green-sensitive layer, a red-sensitive layer, and an infrared-sensitive layer; and a combination of a red-sensitive layer, an infrared-sensitive layer (I), and an infrared-sensitive layer (II), as described, for example, in JP-A Nos. 180550/1984, 13546/1989, 253159/1987, and European Patent Publication No. 479,167. Each of light-sensitive layers can have various configuration orders known for a conventional color photographic light-sensitive material. Further, each of the light-sensitive layers may be divided into two or more layers, as described in JP-A No. 252954/1990, according to the occasion.

In the heat-developable light-sensitive material, various light-insensitive layers, such as a protective layer, a subbing layer, an interlayer, a yellow filter layer, and an antihalation layer, can be set between the above-mentioned silver halide emulsion layers, or as an uppermost layer, or a lowermost layer, on a support. Further, on the reverse side of the support, various supplemental layers, such as a back layer, can be set. Specifically, there can be mentioned a layer construction as described in the above patents, and further a subbing layer, as described in U.S. Pat. No. 5,051,335; an interlayer containing a dispersion of a solid dye, as described in JP-A Nos. 167838/1989 and 20943/1986; an interlayer containing a reducing agent and a DIR compound, as described in JP-A Nos. 120553/1989, 34884/1993, and 64634/1990; an interlayer containing an electron-transferring agent, as described in U.S. Pat. Nos. 5,017,454, and 5,139,919 and JP-A No. 235044/1990; a protective layer containing a reducing agent, as described in JP-A No. 249245/1992, or a combination of these layers, can be set.

When the support is a paper laminated with polyethylene containing a white pigment, such as titanium dioxide, preferably the back layer is designed to have an antistatic function and a surface-specific resistance of $10^{12}$ $\Omega \cdot cm$ or less.

In the present invention, an image-formation accelerator can be added to a heat-developable light-sensitive material. The image-formation accelerator serves to accelerate the redox reaction between a silver salt oxidizer and a reducing agent, and to accelerate such reaction as production or decomposition of a dye from a dye-providing material and release of a diffusible dye from a dye-providing compound. From the standpoint of physicochemical function, the image-formation accelerator can be classified into a nucleophilic compound, a high-boiling-point organic solvent (oil), a heat solvent, a surface-active agent, and a compound that interacts with silver or silver ion. However, these compounds normally have composite functions and exert some of these accelerating effects in combination. These image-formation accelerators are further described in U.S. Pat. No. 4,678,739, columns 38–40.

The hydrophobic additives, such as a dye-providing compound and a diffusion-resistance-reducing agent, can be incorporated in a layer of a heat-developable light-sensitive material according to known methods, as described in U.S. Pat. 2,322,027. In this case, high-boiling-point organic solvents, as described in U.S. Pat. Nos. 4,555,470, 4,536,466, 4,536,467, 4,587,206, 4,555,476, and 4,599,296, and JP-B No. 62256/1991, can be used in combination with a low-boiling-point organic solvent having a boiling point of 50° C. to 160° C., according to the occasion. Further, each of the above-mentioned dye-providing compounds, diffusion-resistance-reducing agents, high-boiling-point organic solvents, and the like may be used as a blend of two or more kinds of compounds.

The amount of the high-boiling-point organic solvent to be used is generally 10 g or less, preferably 5 g or less, and still more preferably in a range of 1 g to 0.1 g, per g of the dye-providing compound, and the amount is also generally 1 cc or less, preferably 0.5 cc or less, and especially 0.3 cc or less, per g of binder.

Further, a polymer dispersion method, as described in JP-B No. 39853/1976 and JP-A No. 59943/1976, and a fine grain dispersion method, as described in JP-A No. 30242/1987, can also be used.

When the hydrophobic additives are substantially water-insoluble compounds, they may be incorporated in a layer as a dispersion of fine grains in a binder, in addition to the above-described methods.

When the hydrophobic compound is dispersed in a hydrophilic colloid, various surface-active agents can be used. For example, those described in JP-A No. 157636/1984, pp. 37–38, and in the above-cited *Research Disclosure*, Section "Surface-Active Agent", can be used.

In the heat-developable light-sensitive material of the present invention, a compound that activates development and at the same time stabilizes an image, can be used. Specific preferable examples of the compound for use in the present invention are described in U.S. Pat. No. 4,500,626, columns 51 to 52.

Examples of hardeners that are used for photographic constructive layers of the heat developable light-sensitive material are described, for example, in the above-cited *Research Disclosure*, U.S. Pat. Nos. 4,678,739, col. 41, and 4,791,042, JP-A Nos. 116655/1984, 245261/1987, 18942/1986, and 218044/1992. Specific examples of the hardener include aldehyde-type hardeners (e.g. formaldehyde), aziridine-type hardeners, epoxy-type hardeners, vinylsulfone type hardeners (e.g. N,N'-ethylene-bis (vinylsulfonylacetamido)ethane), N-methylol-type hardeners (e.g. dimethylol urea), and high-molecular-weight hardeners (e.g. compounds as described, for example, in JP-A No. 234157/1987).

The amount of the hardener to be used is generally in a range of 0.001 to 1 g, and preferably 0.005 to 0.5 g, per 1 g of gelatin coated. The layer to which the hardener is added may be any of photographic constitutive layers of the light-sensitive material or the dye-fixing element. The hardener may be added to two or more separate layers.

The photographic constitutive layers of the heat-developable light-sensitive material may comprise various antifoggants or photographic stabilizers or precursors thereof. Specific examples of these compounds are disclosed, for example, in the above-cited RD's, U.S. Pat. Nos. 5,089,378, 4,500,627, and 4,614,702; JP-A No. 13546/1989, pp. 7–9, 57–71, and 81–97; U.S. Pat. Nos. 4,775,610, 4,626,500, and 4,983,494; JP-A Nos. 174747/1987, 239148/1987, 264747/1988, 150135/1989, 110557/1990, 178650/1990, and RD 17643 (1978), pp. 24–25.

These compounds are preferably used in an amount of $5 \times 10^{-6}$ to $1 \times 10^{-1}$ mol, and more preferably $1 \times 10^{-5}$ to $1 \times 10^{-2}$ mol, per mol of silver.

The photographic constitutive layers of the heat-developable light-sensitive material can comprise various surface-active agents for aiding coating, improving peelability and slip properties, inhibiting electrification, accelerating development, or like purposes. Specific examples of the surface-active agent are described, for example, in the above cited RD's, JP-A Nos. 173463/1987, and 183457/1987.

The photographic constitutive layers of the heat-developable light-sensitive material can comprise an organic fluoro compound incorporated therein, for improving slip properties and peelability, inhibiting electrification, or like purposes. Representative examples of the organic fluoro compound include fluoro surface-active agents, and hydrophobic fluorine compounds, such as oil fluorine compounds (e.g. fluorine oil) and solid fluorine compound resins (e.g. ethylene tetrafluoride resin), as described, for example, in JP-B No. 9053/1987, column 8 to 17, JP-A Nos. 20944/1986, and 135826/1987.

The heat-developable light-sensitive material can comprise a matting agent for preventing adhesion, improving slip properties, and making a non-glossy surface. Example matting agents are described in JP-A Nos. 274944/1988 and 274952/1988, including benzoguanamine resin beads, polycarbonate resin beads, and AS resin beads, in addition to compounds described in JP-A No. 88256/1986, p. 29, including silicon dioxide, polyolefin, and polymethacrylate. Other example matting agents are described in the above-cited RD's. These matting agents can be added not only to an uppermost layer (protective layer) but also to an under layer, according to the occasion.

Additionally, the photographic constructive layers of the heat-developable light-sensitive material may comprise a heat solvent, an antifoaming agent, a bacteriocide, a mildew-proofing agent, a colloidal silica, etc. Specific examples of these additives are described in, for example, JP-A No. 88256/1986, pp. 26–32, JP-A No. 11338/1991, and JP-B No. 51496/1990.

Examples of the support that can be used in the photographic light-sensitive material of the present invention include synthetic plastic films, such as polyolefins (e.g. polyethylene, polypropylene), polycarbonates, cellulose-acetate, polyethylene terephthalate, polyethylene naphthalates, and polyvinyl chloride; paper supports, such as a photographic raw paper, a print paper, a baryta paper, and a resin-coated paper; a support having a reflective layer on the above-described synthetic plastic film; and a support described in JP-A No. 253159/1987, pp. 29–31.

A support having minimized core-set-curl can be obtained by subjecting the support to heat treatment at a temperature not higher than the support's Tg, as described in U.S. Pat. No. 4,141,735. Further, the surface of the support may be subjected to surface treatment, in order to improve adhesion between the support and a subbing layer for an emulsion. In the present invention, a glow discharge treatment, an ultraviolet-ray-irradiation treatment, a corona discharge treatment, and a flame treatment can be preferably used as the surface treatment.

Further, the support described in Kochi Gijutsu, Vol. 5 (published by Azutec L.R. Co., Mar. 22, 1991), pp. 144–149, can also be used.

In the present invention, various development stop agents can be incorporated in the heat-developable light-sensitive material, for the purpose of obtaining an invariably constant image quality against the fluctuation of processing temperature and time during development. The term "development stop agent" used herein means a compound that rapidly neutralizes or reacts with a base after a proper development, to reduce the base concentration in the film to stop development, or a compound that interacts with silver or a silver salt after a proper development, to inhibit development. Specific examples of the development stop agent include an acid precursor that is able to release an acid under heat, an electrophilic compound that undergoes substitution reaction with a base present therewith under heating, a nitrogen-containing heterocyclic compound, a mercapto compound, and precursors thereof. These compounds are further described in JP-A No. 253159/1987, pp. 31–32.

Further, the light-sensitive element may have additional layers ordinarily employed in the field of this technology, such as a spacer layer, a layer containing a halation-preventing dye, and/or a filter dye layer positioned between silver halide emulsion layers, each having a different spectral sensitive region. A protective layer may be set in an image-recording material of the present invention. The protective layer may contain various additives ordinarily employed in the field of photographic art. Suitable additives include a matting agent, colloidal silica, a sliding agent, an organic fluoro compound, a UV absorber, an accelerator, a fine-grain silver halide, an antioxidizing agent, and paradium chloride.

Examples of the method for image-wise exposing the heat-developable light-sensitive material, to record an image thereon, include a method that comprises directly photographing a scene or persons by means of a camera, etc.; a method that comprises exposure through a reversal film or negative film by means of a printer or enlarger, etc.; a method that comprises scanning exposure to an original image through a slit and the like by means of an exposing apparatus in a photocopier, etc.; a method that comprises scanning exposure to light emitted by a light-emitting diode or various lasers (e.g. laser diodes, gas lasers) excited by an electrical signal representative of image data, as described, for example, in JP-A No. 129625/1990, and Japanese Patent Application Nos. 338182/1991, 9388/1992, and 281442/1992; and a method that comprises exposure directly or through an optical system to image data outputted to an image display apparatus, such as a CRT, a liquid crystal display, an electroluminescence display, and a plasma display.

Example light sources to be used for recording an image on the heat-developable light-sensitive material are described in U.S. Pat. No. 4,500,626, column 56, JP-A Nos. 53378/1990, and 54672/1990, such as natural light, a tungsten lamp, light-emitting diodes, laser light sources, and CRT light sources.

Further, a light source that uses of blue-light-emitting diodes, which are recently making great progress, in combination with green-light-emitting diodes and red-light-emitting diodes can be also used. In particular, exposure devices described in Japanese Patent Application Nos. 40164/1994, 40012/1994, 42732/1994, 86919/1994, 86920/1994, 93421/1994, 94820/1994, 96628/1994, and 149609/1994 can be preferably used.

Further, an image-wise exposure to light can be conducted by the use of a wavelength conversion element, in which a nonlinear optical material is combined with a coherent light source, such as laser light and the like. The term "nonlinear optical material" herein used means a material capable of providing a nonlinear optical property between the polarization and electric field created when a strong photoelectric field, such as a laser light, is given. Inorganic compounds, such as lithium niobate, potassium dihydrogenphosphate (KDP), lithium iodate, and $BaB_2O_4$; urea derivatives, nitroaniline derivatives, nitropyridine-N-oxide derivatives, such as 3-methyl-4-nitropyridine-N-oxide (POM); and compounds described in JP-A Nos. 53462/1986 and 210432/1987, are preferably used. Known forms of the wavelength conversion element are a single crystal light waveguide path-type wavelength conversion element, a fiber-type wavelength conversion element, and the like. Any of these types of the wavelength conversion element can be effectively used.

Further, examples of the image data that the present invention can be applied to include image signals obtained from a video camera, an electronic still camera, and the like; television signals stipulated by the National Television Signal Code (NTSC); image signals obtained by dividing an original image into many pixels by means of a scanner, etc.; and image signals produced by means of a computer, with typical examples being CG and CAD.

The heat-developable light-sensitive material of the present invention may comprise an electrically conductive heat-generation-element layer as a heating means for heat development. The heat-generation elements described in JP-A No. 145544/1986 can be used.

The heating temperature at the heat-developing process is approximately in the range of 80° C. to 180° C., preferably 80° C. to 150° C., and more preferably 80° C. to 135° C. The heating time is generally in the range of 0.1 to 60 seconds, and preferably 0.1 to 30 seconds.

Examples of the heating means at the developing process include a method that comprises bringing the light-sensitive material into contact with a heated block or plate, or alternatively with a hot plate, a hot presser, a heat roller, a hot drum, a halogen lamp heater, or an infrared or far infrared lamp heater; and a method that comprises passing the light-sensitive material through a high-temperature atmosphere.

As a process for the lamination of the heat-developable light-sensitive material and the dye-fixing element, a process described in JP-A No. 253159/1987 and JP-A No. 147244/1986, page 27 can be used.

The processing, when the compound according to the present invention is incorporated in a silver halide light-sensitive material for an activator processing, is explained below in detail. In the present invention, the light-sensitive material is subjected to development (cross oxidation of silver development/the incorporated reducing agent), desilvering, and washing with water or stabilization. Further, the washing or the stabilization may be followed by a process for strengthening color formation with an alkali bath and the like.

At the time of development of the light-sensitive material in the present invention, the developing solution contains a compound that works as a developing agent of silver halide, and/or, as a result of the silver development, the development solution contains an oxidation product that is able to cross oxidize the reducing agent for color formation, which reducing agent is incorporated in the light-sensitive material. Preferred examples of the compound include pyrazolidones, dihydroxybenzenes, reductons, and aminophenols. In particular, the pyrazolidones are preferably used.

As the pyrazolidones, 1-phenyl-3-pyrazolidones are preferred with specific examples including 1-phenyl-3-pyrazolidone, 1-phenyl-4,4-dimethyl-3-pyrazolidone, 1-phenyl-4-methyl-4-hydroxymethyl-3-pyrazolidone, 1-phenyl-4,4-dihydroxymethyl-3-pyrazolidone, 1-phenyl-5-methyl-3-pyrazolidone, 1-phenyl-5-phenyl-3-pyrazolidone, 1-p-toryl-4-methyl-4-hydroxymethyl-3-pyrazolidone, 1-p-chlorophenyl-4-methyl-4-hydroxymethyl-3-pyrazolidone, 1-phenyl-2-hydroxymethyl-4,4-dimethyl-3-pyrazolidone, 1-phenyl-2-acetyl-3-pyrazolidone, and 1-phenyl-2-hydroxymethyl-5-phenyl-3-pyrazolidone.

Examples of the dihydroxybenzenes include hydroquinone, chlorohydroquinone, bromohydroquinone, isopropylhydroquinone, methylhydroquinone, 2,3-dichlorohydroquinone, 2,5-dichlorohydroquinone, 2,5-dimethylhydroquinone, and potassium hydroquinone monosulfonate.

As the reductons, ascorbic acid and its derivatives are preferred, and compounds described in JP-A No. 148822/1994, pp. 3–10, can be used. In particular, sodium L-ascorbate and sodium erysorbate are preferred.

Examples of the p-aminophenols include N-methyl-p-aminophenol, N-(β-hydroxyethyl)-p-aminophenol, N-(4-hydroxyphenyl)glycine, and 2-methyl-p-aminophenol.

These compounds are ordinarily used alone, but it is preferred to use two or more kinds of these compounds in combination in order to strengthen the activities of development and cross oxidation.

The amount of these compounds to be used in a developing solution is generally in a range of $2.5 \times 10^{-4}$ mol/l to 0.2 mol/l, preferably 0.0025 mol/l to 0.1 mol/l, and more preferably 0.001 mol/l to 0.05 mol/l.

The developing solution used for the present invention further contains various preservatives, such as sodium sulfite, potassium sulfite, lithium sulfite, ammonium sulfite, sodium bisulfite, potassium methabisulfite, formaldehyde/sodium-bisulfite adduct, and hydroxylamine sulfate salt. The amount of the preservative to be used is generally not more than 0.1 mol/l, and preferably the amount is in the range of 0.001 to 0.02 mol/l. When a high silver-chloride-content emulsion is used for the light-sensitive material, the amount of the preservative to be used is generally not more than 0.001 mol/l, and sometimes the developing solution preferably has no content at all the above-described preservatives.

In the present invention, it is preferred to use an organic preservative in place of the above-mentioned hydroxylamine and sulfite ions.

The term "organic preservative" used herein means all of the organic compounds that are able to reduce the deterioration speed of the above-described developing agent, when added to a developing solution. That is, they are organic compounds that function to prevent the developing agent from oxidation by air, etc. Especially effective organic preservatives are hydroxylamine derivatives (excluding hydroxylamine itself) hydroxamic acids, hydrazines, phenols, α-hydroxyketones, α-aminoketones, saccharides, monoamines, diamines, polyamines, quaternary ammonium compounds, nitroxyl radicals, alcohols, oximes, diamide compounds, and condensed cyclic amines. These compounds are described, for example, in JP-A Nos. 4235/1988, 5341/1988, 30845/1988, 21647/1988, 44655/1988, 46454/1988, 53551/1988, 43140/1988, 56654/1988, 58346/1988, 43138/1988, 146041/1988, 44657/1988, 44656/1988, and U.S. Pat. Nos. 3,615,503, 2,494,903, and JP-B No. 30496/1973. Additionally, various metals, as described in JP-A Nos. 44148/1982 and 53749/1982; salicylic acids, as described in JP-A No. 180588/1984; alkanolamines, as described in JP-A No. 3532/1979; polyethyleneimines, as described in JP-A No. 94349/1981; and aromatic polyhydroxy compounds, as described in U.S. Pat. No. 3,746,544, may be used as a preservative, according to the occasion. It is especially preferred to use alkanolamines, as described in JP-A No. 97355/1992, pp. 631–632, and dialkylhydroxylamines, as described in JP-A No. 97355/1992, pp. 627–630. Further, it is also preferred to use dialkylhydroxylamines, and/or hydrazine derivatives and alkanolamines in combination, or to use dialkylhydroxylamines, as described in EPO 530921A1, and α-amino acids, represented by glycine, in combination.

The amount of these compounds to be used is preferably in the range of $1\times10^{-3}$ to $5\times10^{-1}$ mol, more preferably $1\times10^{-2}$ to $2\times10^{-1}$ mol, per liter of the developing solution.

In the present invention, the developing solution contains halide ions, such as chloride ions, bromide ions, and iodide ions. Preferably, when a high silver-chloride emulsion is used, chloride ions are contained in an amount of $3.5\times10^{-3}$ to $3.0\times10^{-1}$ mol/liter, and more preferably $1\times10^{-2}$ to $2\times10^{-1}$ mol/liter, and/or bromide ions in an amount of $0.5\times10^{-5}$ to $1.0\times10^{-3}$ mol/liter, and more preferably $3.0\times10^{-5}$ to $5\times10^{-4}$ mol/liter.

Herein the halide ions may be added directly to the developing solution, or they may be dissolved out from the photographic material into the developing solution during the development processing.

If the halide ions are added to the developing solution, the halide ion source may be a sodium salt, a potassium salt, an ammonium salt, a lithium salt, or a magnesium salt, of the halide ion.

When the halide ions are dissolved out from the photographic material, the halide ions are supplied mainly from the silver halide emulsion, but they may also be supplied from some other source.

The developing solution used in the present invention preferably has a pH of 8 to 13, and more preferably 9 to 12.

To retain the above pH, it is preferable to use various buffers, examples of which are carbonates, phosphates, brorates, tetraborates, hydroxybenzoates, glycinates, N,N-dimethylglycinates, leucinates, norleucinates, guaninates, 3,4-dihydroxyphenylalaninates, alaninates, aminobutylates, 2-amino-2-methyl-1,3-propandiol salts, valerates, prolinates, trishydroxylaminomethane salts, and lysinates. In particular, carbonates, phosphates, tetraborates, and hydroxybenzoates are excellent in solubility and buffering function at a pH in the range of 9.0 or over, and when they are added to the developing solution, the photographic performance is not adversely affected, so that they are preferably used.

Specific examples of these buffers are lithium carbonate, sodium carbonate, potassium carbonate, potassium bicarbonate, tripotassium phosphate, trisodium phosphate, dipotassium phosphate, disodium phosphate, potassium borate, sodium borate, sodium tetraborate, potassium tetraborate, sodium o-hydroxybenzoate (sodium salicylate), and potassium 5-sulfo-2-hydroxybenzoate (potassium 5-sulfosalicylate).

The amount of the buffers to be added to the developing solution is preferably 0.05 mol/liter or over, and particularly preferably 0.1 to 0.4 mol/liter.

In addition, in the developing solution, as a sediment-preventive agent against calcium and magnesium, or as an agent for stabilizing the developing solution, various chelating agents can be used. Examples are nitrilotriacetic acid, diethylenetriaminepentaacetic acid, ethylenediaminetetraacetic acid, N,N,N-trimethylenephosphonic acid, ethylenediamine-N,N,N',N'-tetramethylenesulfonic acid, 1,2-diaminopropanetetraacetic acid, glycol ether diaminetetraacetic acid, ethylenediamine orthohydroxyphenylacetic acid, 2-phosphonobutane-1,2,4-tricarboxylic acid, 1-hydroxyethylidene-1,1-diphosphonic acid, and 1,2-dihydroxybenzene-4,6-disulfonic acid, and their alkali metal salts. Two or more of these chelating agents may be used in combination, if necessary.

With respect to the amount of these chelating agents to be added, preferably the amount is enough to sequester the metal ions in the developing solution, and, for example, these chelating agents are used in an amount in the order of 0.1 to 10 g per liter.

In the present invention, if required, an arbitrary antifoggant can be added. As the antifoggant, nitrogen-containing heterocyclic compounds, and alkali metal halide, such as sodium chloride, potassium bromide, and potassium iodide, are used. Typical examples of the nitrogen-containing heterocyclic compounds are benzotriazole, 5-nitrobenzotriazole, 5-methylbenzotriazole, 6-nitrobenzimidazole, 5-nitroisoimidazole, 2-thiazolylbenzimidazole, indazole, hydroxyazaindolizine, adenine, and 1-phenyl-5-mercaptotetrazole, or their derivatives.

The amount of the nitrogen-containing heterocyclic compounds to be added is $1\times10^{-5}$ to $1\times10^{-2}$ mol/liter, and preferably $2.5\times10^{-5}$ to $1\times10^{-3}$ mol/liter.

In the developing solution, if necessary, an arbitrary development accelerator can be added, examples of which are the following compounds: thioether compounds described, for example, in JP-B Nos. 16088/1962, 5987/1962, 7826/1963, 12380/1969, and 9019/1970, and U.S. Pat. No. 3,813,247; p-phenylenediamine compounds described in JP-A Nos. 49829/1977 and 15554/1975; quaternary ammonium salts described, for example, in JP-A No. 137726/1975, JP-B No. 30074/1969, and JP-A Nos. 156826/1981 and 43429/1977; amine compounds described, for example, in U.S. Pat. Nos. 2,494,903, 3,128,182, 4,230,796, and 3,253,919, JP-B No. 11431/1966, and U.S. Pat. Nos. 2,482,546, 2,596,926, and 3,582,346; and imidazoles and polyalkylene oxides described, for example, in JP-B Nos. 16088/1962, 25201/1967, U.S. Pat. No. 3,128,183, JP-B Nos. 11431/1966 and 23883/1967, and U.S. Pat. No. 3,532, 501.

Preferably the developing solution contains a fluorescent whitening agent. In particular, it is preferable to use 4,4'-diamino-2,2'-disulfostilbene-type compounds. Specifically, commercially available fluorescent whitening agents, such as compounds described, for example, in "Senshoku Note," 19th edition, pages 165 to 168, and compounds described in JP-A No. 242943/1992, pages 3 to 7, can be used. The amount to be added is 0.1 to 10 g/liter, and preferably 0.5 to 5 g/liter.

The processing temperature of the developing solution to be applied to the present invention is 20 to 50 ° C., and preferably 30 to 45 ° C. The processing time is 5 sec to 2 min, and preferably 10 sec to 1 min. With respect to the replenishing rate, although a small amount is preferable, the replenishing rate is 15 to 600 ml, preferably 25 to 200 ml, and more preferably 35 to 100 ml, per m² of the photographic material.

After development, preferably the light-sensitive material is subjected to a desilvering processing. The desilvering processing may be a fix processing or a bleach-and-fix processing. In the bleach-and-fix processing, the bleach processing and the fix processing may be conducted separately or simultaneously (the latter processing is called a blix processing). Further, the desilvering may be performed by processing with two blix baths in succession, or by fixing before the blix processing, or by bleaching after the blix processing, in accordance with its object.

Further, when the occasion demands, it is also preferred to stabilize a silver image and a color image by conducting a stabilization processing without the desilvering after the development.

Example bleaching agents for use in the bleaching solution or the bleach-fix(blix) solution include, for example, compounds of polyvalent metals, such as iron(III), cobalt (III), cromium(IV), and copper(II); peracids; qunones; and nitro compounds. Typical compounds are iron chloride, ferricyanides, dichromates, organic complex salts of iron (III) (e.g. metal salts of ethylenediaminetetraacetic acid, diethylenetriaminepentaacetic acid, cyclohexanediaminetetraacetic acid, 1,3-diaminopropanetetraacetic acid, methylimiodiacetic acid; and aminopolycarboxylic acids and their salts, as described in JP-A No. 365036/1992, pages 5 to 17), persulfates, permanganates, bromates, hydrogen peroxide and compounds releasing thereof (e.g. percarbonic acid and perboric acid), and nitrobenzenes. Among them, ethylenediaminetetraacetatic acid iron(III) complex salts, aminopolycarboxylic acid iron(III) of 1,3-diaminopropanetetraacetate iron(III) complex salts, hydrogen peroxide, persulfates, and the like are preferred, in view of rapid processing and the prevention of enviromental pollution. The bleaching solution and bleach-fix solution that use these aminopolycarboxylic acid irons(III) are used at a pH of 3 to 8, and preferably 5 to 7. The bleaching solution that uses persulfates and hydrogen peroxide is used at a pH of 4 to 11, and preferably 5 to 10.

In the bleaching solution, the bleach-fix solution, and the bath preceding them, if required, a bleach-accelerating agent can be used. Specific examples of useful bleach-accelerating agents include compounds having a mercapto group or a disulfide bond, as as described, for example, in U.S. Pat. No. 3,893,856, West German Patent No. 1,290,812, JP-A No. 95630/1978, and Research Disclosure No. 17129 (July 1978); thiazolidine derivatives described in JP-A No. 140129/1975; thiourea derivatives described in U.S. Pat. No. 3,706,561; iodide salts described in JP-A No. 16235/1983; polyoxyethylene compounds described in West Germany Patent No. 2,748,430; and iodide ions and polyamine compounds described in JP-B No. 8836/1970.

Above all, compounds having a mercapto group or a disulfide group are preferable, because they are high in accelerating effect. When color photographic materials for photography are desilvered, these bleach-accelerating agents are particularly effective.

With respect to the accelerating agent for persulfate bleaching, complex salts of 2,6-pyridinedicarboxylic acid or 2-pyridinecarboxylic acid with iron (III) ion, as described in JP-A No. 214365/1994 (European Patent No. 0602600A1), are effective. With respect to the accelerating agent for hydrogen peroxide bleaching, metal complex salts of organic acids, described in JP-B Nos. 16067/1986 and 19024/1986, are effective.

In the bleaching solution, the bleach-fix solution, and the fixing solution, use can be made of known additives, such as a rehalogenating agent, including ammonium bromide and ammonium chloride; a pH buffering agent, including ammonium nitrate, acetic acid, boric acid, citric acid or its salt, tartaric acid or its salt, succinic acid or its salt, and imidazole; and a metal corrosion-preventive agent, including ammonium sulfate. In particular, it is preferable to contain an organic acid, to prevent bleach stain. The organic acid is a compound having an acid dissociation constant (pKa) of 2 to 7, and specifically acetic acid, succinic acid, citric acid, and propionic acid are preferable.

Example fixing agents for use in the fixing solution and the bleach-fix solution include thiosulfates, thiocyanates, thioureas, a large amount of iodide salts, and thioether compounds, metho-ionic compounds, and nitrogen-containing heterocyclic compounds, having a sulfide group, as described in JP-A No. 365037/1992, pages 11 to 21, and JP-A No. 66540/1993, pages 1088 to 1092. Among these, use of thiosulfates is usual, and ammonium thiosulfate is most widely used. A combination of thiosulfates with thiocyanates, thioether compounds, thiourea, or metho-ionic compounds, is also preferable.

Preferable preservatives for the fixing solution and the bleach-fix solution are sulfites, bisulfites, carbonylbisulfite adducts, and sulfinic acid compounds described in European Patent No. 294769A. In the fixing solution, the bleaching solution, and the bleach-fix solution, to stabilize the solutions, it is preferable to add any of various aminopolycarboxylic acids, organic phosphonic acids (e.g. 1-hydroxyethylidene-1,1-diphosphonic acid, N,N,N',N'-ethylenediaminetetraphosphonic acid, and 2-phosphonobutane-1,2,4-ticarboxylic acid) and sodium stannate.

In the fixing solution and the bleach-fix solution, further, for example, any of various fluorescent whitening agents, antifoaming agents, surface-active agents, polyvinylpyrolidones, and methanol can be contained.

The processing temperature of the desilvering step is 20° to 50° C., and preferably 30° to 45° C. The processing time is 5 sec to 2 min, and preferably 10 sec to 1 min. Although a small replenishing rate is preferable, the replenishing rate is 15 to 600 ml, preferably 25 to 200 ml, and more preferably 35 to 100 ml, per m² of the photographic material. The processing is also preferably carried out without replenishment in such a way that the evaporated amount is supplemented with water.

The photographic material of the present invention is generally passed through a washing (rinsing) step after the desilvering process. If a stabilizing process is carried out, the washing step can be omitted. In such a stabilizing process, processes described in JP-A Nos. 8543/1982, 14834/1983, and 220345/1985, and all known processes described in JP-A Nos. 127926/1983, 137837/1983, and 140741/1983, can be used. A washing-stabilizing process, in which a stabilizing bath containing a dye stabilizer and a surface-active agent typically used for the processing of color photographic materials for photographing is used as a final bath, can be carried out.

In the washing liquid and stabilizing solution, use can be made of a water softener, such as sulfites, inorganic phosphoric acids, polyaminocarboxylic acids, and organic aminophosphoric acids; a metal salt, such as Mg salts, Al salts, and Bi salts; a surface-active agent, a hardener, a pH buffer, a fluorescent whitening agent, and a silver-salt-forming agent, such as nitrogen-containing heterocyclic compounds.

Example dye-stabilizing agents of the stabilizing solution include, for example, aldehydes, such as formaldehyde and glutaraldehyde; N-methylol compounds, hexamethylenetetramine, or aldehyde sulfite adducts.

The pH of the washing liquid and the stabilizing solution is 4 to 9, and preferably 5 to 8. The processing temperature is 15° to 45° C., and preferably 25° to 40°. The processing time is 5 sec to 2 min, and preferably 10 sec to 40 sec.

The overflow liquid associated with the replenishment of the above washing liquid and/or the stabilizing solution, can be reused in other processes, such as the desilvering process.

The amount of the washing liquid and/or the stabilizing solution can be set in a wide range depending on various conditions, and the replenishing rate is preferably 15 to 360 ml, and more preferably 25 to 120 ml, per $m^2$ of the photographic material. To reduce the replenishing rate, it is preferable to use multiple tanks and a multi-stage countercurrent system. In particular, it is preferable to use 2 to 5 tanks. In order to prevent the propagation of bacteria and adhesion stain of suspended matter on the photographic material that will result from reduction in the amount of these solutions, use can be made of bactericides, such as sodium chlorinated isocynurate, cyapentazoles, and isothiazolone compounds described in JP-A No. 8542/1982; other benzotriazoles; and bactericides described by Hiroshi Horiguchi in "Bokin- bobaizai no Kagaku" (1986, Sankyoshuppan); in "Biseibutsu no Mekkin, Sakkin, Bobai Gijutsu," edited by Eisei Bobai-gakkai (1982, Kogyo Gijutsu-kai); and in "Bokin Babai-zai Jiten," edited by Nihon Bokin Bobai-gakkai (1986). Further, a method of reducing Mg and Ca ions, as described in JP-A No. 288838/1987, is particularly preferably used.

In the present invention, in order to save water, water can be used that has been obtained by treating the overflow liquid or the in-tank liquid using a reverse osmosis membrane. For example, the treatment by reverse osmosis is preferably carried out for water from the second tank, or the more latter tank of the multi-stage countercurrent washing process and/or the stabilizing process. Specifically, in the case of a two-tank system, the water in the second tank is treated by a reverse osmosis membrane, and in the case of a four-tank system, the water in the third tank and the fourth tank is treated by a reverse osmosis membrane, and then the passed water is returned to the same tank (the tank from which water for the reverse osmosis treatment has been taken) or is brought to a washing tank and/or a stabilizing tank situated downstream. It is also one mode that the concentrated liquid is returned to a tank situated upstream of that particular tank and further to the desilvering bath.

As the material of the reverse osmosis membrane, for example, cellulose acetates, crosslinked polyamides, polyethers, polysulfons, polyacrylic acids, and polyvinylene carbonates can be used. The pressure of the pumped liquid used for these membranes is preferably 2 to 10 $kg/cm^2$ and particularly preferably 3 to 7 $kg/cm^2$.

In the present invention, preferably the stirring is intensified as much as possible. To intensify the stirring, specifically a method wherein a jet stream of a processing liquid is caused to impinge on the emulsion surface of a photographic material, as described in JP-A Nos. 183460/1987 and 183461/1987; a method wherein a rotating means is used to increase the stirring effect, as described in JP-A No. 183461/1987; a method wherein a photographic material is moved, with the emulsion surface of the material being in contact with a wiper blade provided in a liquid, so that a turbulent flow may occur near the emulsion surface, to improve the stirring effect; and a method wherein the total amount of a processing solution to be circulated is increased, can be mentioned. These means of improving the stirring are useful in any of the developing solution, the bleaching solution, the fixing solution, the bleach-fix solution, the stabilizing solution, and the washing liquid. These methods are effective in that the effective constituents in the solution are supplied to the photographic material and the diffusion of unnecessary components in the photographic material is promoted.

In the present invention, any state of the liquid opening rate [contact area of air $(cm^2)$/liquid volume $(cm^3)$] of any of the baths can exhibit excellent performance, but in view of the stability of the liquid components, preferably the liquid opening rate is 0 to 1.0 $cm^{-1}$. In the continuous processing, from a practical point of view, the liquid opening rate is preferably 0.001 to 0 05 $cm^{-1}$, and more preferably 0.002 to 0.03 $cm^{-1}$.

The automatic developing machine used for the photographic material of the present invention is preferably provided with a means of transporting a photographic material, as described in JP-A No. 191257/1985, 191258/1985, and 191259/1985. Such a transporting means can reduce remarkably the carry-in of the processing solution from a preceding bath to a succeeding bath. Therefore it is high in the effect of preventing the performance of a processing solution from being deteriorated. Such an effect is effective in shortening the processing time of each process and in reducing the process replenishing rate. To shorten the processing time, it is preferable to shorten the crossover time (the aerial time), and a method wherein a photographic material is transported between processes through a blade having a screening effect, as described, for example, in JP-A No. 86659/1992, FIG. 4, 5, or 6, and JP-A No. 66540/1993, FIG. 4 or 5, is preferable.

Further, if each of the processing solutions in the continuous process is concentrated due to evaporated, preferably water is added to compensate for the evaporation.

The processing time in each process according to the present invention means the time required from the start of the processing of the photographic material at any process, to the start of the processing in the next process. The actual processing time in an automatic developing machine is determined generally by the linear speed and the volume of the processing bath, and in the present invention, as the linear speed, 500 to 4,000 mm/min can be mentioned as a guide. Particularly in the case of a small-sized developing machine, 500 to 2,500 mm/min is preferable.

The processing time in the whole processing steps, that is, the processing time from the developing process to the drying process, is preferably 360 sec or below, more preferably 120 sec or below, and particularly preferably 90 to 30 sec. Herein the processing time means the time from the dipping of the photographic material into the developing solution, till the emergence from the drying part of the processor.

Processing methods and components that are used when the silver halide light-sensitive material is processed with a developing solution containing the compound according to the present invention, are explained below in details.

The color-developing agent of the present invention can be used alone, or with other known p-phenylenediamine derivatives in combination. Typical examples of the compounds to be used in combination are illustrated below, but the present invention is not restricted thereto.

P-1 N,N-diethyl-p-phenylenediamine
P-2 4-amino-3-methyl-N,N-diethylaniline

P-3 4-amino-3-methyl-N-ethyl-N-(3-hydroxypropyl)aniline
P-4 4-amino-N-ethyl-N-(2-hydroxyethyl)aniline
P-5 4-amino-3-methyl-N-ethyl-N-(2-hydroxyethyl)aniline
P-6 4-amino-3-methyl-N-ethyl-N-(2-methanesulfonamidoethyl)aniline
P-7 N-(2-amino-5-N,N-diethyl-aminophenylethyl)methanesulfonamide
P-8 N,N-dimethyl-p-phenylenediamine
P9 4-amino-3-methyl-N-ethyl-N-(2-methoxyethyl)aniline
P-10 4-amino-3-methyl-N-ethyl-N-(4-hydroxybutyl)aniline
P-11 4-amino-3-methyl-N-ethyl-N-(2-butoxyethyl)aniline As a compound to be used in combination, P-3, P-5, P-6, and P-10 are especially preferred, of the above-described p-phenylenediamine derivatives. These p-phenylenediamine derivatives are generally used in the form of a salt, such as a sulfate, a hydrochloride, a sulfite, a p-toluenesulfonate, a nitrate, and a naphthalene-1,5-disulfonate. Two or more kinds of these compounds may be used in combination, according to the purpose. The amount of the aromatic primary amine developing agent to be used is preferably in a range of 0.001 mol to 0.2 mol, and more preferably 0.005 mol to 0.1 mol, per liter of the color-developing solution.

To the developing solution for use in the present invention, added, as a compound that directly preserves the above-described color-developing agent, are various hydroxylamines, as described in JP-A Nos. 5341/1988, 106655/1988, and 144446/1992; hydroxyamic acids, as described in JP-A No. 43138/1988; hydrazines and hydrazides, as described in JP-A No. 146041/1988; phenols, as described in JP-A Nos. 44657/1988 and 58443/1988; α-hydroxyketones and α-aminoketones, as described in JP-A No. 44656/1988; and saccharides, as described in JP-A No. 36244/1988. Further, in combination with the above-described compounds, use can be made of monoamines, as described, for example, in JP-A Nos. 4235/1988, 24254/1988, 21647/1988, 146040/1988, 27841/1988, and 25654/1988; diamines, as described, for example, in JP-A Nos. 30845/1988, 14640/1988, and 43139/1988; polyamines, as described in JP-A Nos. 21647/1988, 26655/1988, and 44655/1988; nitroxyl radicals, as described in JP-A No. 53551/1988; alcohols, as described in JP-A Nos. 43140/1988, and 53549/1988; oximes, as described in JP-A No. 56654/1988; and tertiary amines, as described in JP-A No. 239447/1988.

Additionally, as a preservative, various metals, as described in JP-A Nos. 44148/1982 and 53749/1982; salicylic acids, as described in JP-A No. 180588/1984; alkanolamines, as described in JP-A No. 3582/1984; polyethyleneimines, as described in JP-A No. 94349/1981; and aromatic polyhydroxy compounds, as described in U.S. Pat. No. 3,746,544, can be used, according to the occasion. When the hydroxylamines are used, in particular, preferably the above-described alkanolamines or aromatic polyhydroxy compounds are used in combination.

Especially preferred preservatives are the hydroxylamines represented by general formula (I) in JP-A No. 144446/1991. The compounds having a methyl group, an ethyl group, a sulfo group, or a carboxy group are most preferred. The amount of these preservatives to be used is generally in the range of 20 millimols to 200 millimols, and preferably 30 millimols to 150 millimols, per liter of the color-developing solution.

Additionally, with respect to such additives as a buffer agent, a chelating agent, an antifoggant, and a development-inhibiting agent; and with respect to the replenishment amount of the developing solution, the processing temperature, the processing time, the reproduction process, desilvering, and washing or stabilization processing, those as described in the explanation of the activator processing are applied thereto.

By using the compound according to the present invention, clear color image can be formed in a short time even under mild conditions.

EXAMPLE

The present invention is explained below in detail with working examples thereof, but the present invention should not be restricted thereto.

Example 1

A preparation of the light-sensitive silver halide emulsion is described.

To a well-agitated aqueous gelatin solution, which had been prepared by adding 31.6 g of gelatin, 2.5 g of potassium bromide, and 13 mg of Compound (a) to 584 ml of water, followed by heating, and the resulting mixture was at 70° C., addition of the liquid (2) shown in Table 1 was begun, and 10 seconds later, addition of the liquid (1) was begun. After that, the liquids (1) and (2) were added over a period of 30 minutes. Further, five minutes after completion of the addition of the liquid (2), addition of the liquid (4) shown in Table 1 was begun, and then 10 seconds later, addition of the liquid (3) was begun. After that, the liquid (3) and the liquid (4) were added over respective periods of 27 minutes and 50 seconds, and 28 minutes. To the reaction mixture, which had been washed and desalted by the precipitating agent (c) at pH 3.9 according to an ordinary method, 24.6 g of lime-treated osein gelatin and 56 mg of Compound (b) were added, and then the pH value and the pAg value of the resulting mixture were adjusted to 6.1 and 8.5, respectively. Further, 0.55 mg of sodium thiosulfate was added to the resulting mixture, whereby optimal chemical sensitization was performed at 65° C. After that, 0.35 g of a sensitizing dye (f), 56 mg of an antifoggant (d), and 2.3 ml of a Compound (e), as an antiseptic, were added to the chemically sensitized emulsion, and then the emulsion was cooled to room temperature, whereby 582 g of monodispersed octahedral silver bromide emulsion, having a mean grain size of 0.55 μm, was obtained.

TABLE 1

|  | Liquid (1) | Liquid (2) | Liquid (3) | Liquid (4) |
| --- | --- | --- | --- | --- |
| $AgNO_3$ | 15.8 g | — | 72.2 g | — |
| $NH_4No_3$ | 68.0 mg | — | 308 mg | — |
| KBr | — | 11.4 g | — | 52.2 g |
| Final Amount | Water to make 134 ml | Water to make 134 ml | Water to make 194 ml | Water to make 195 ml |

TABLE 1-continued

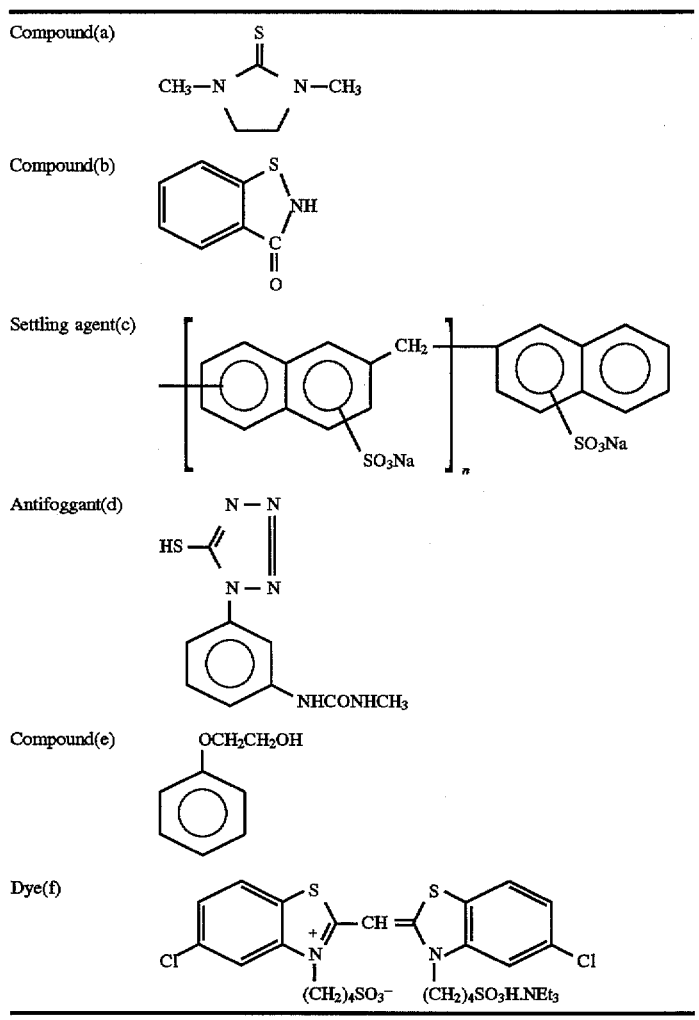

A preparation of silver benzotriazole is described.

6.5 g of benzotriazole and 10 g of gelatin were dissolved in 1 liter of water and kept at 50° C. and agitated. After that, a solution of 8.5 g of silver nitrate in 100 ml of water was added to the above-described solution, over a period of 2 minutes. The thus obtained emulsion was precipitated by adjusting the pH value of the emulsion, to remove a superfluous salt. The pH value of the resulting emulsion was adjusted to 6.0, whereby 400 g (yield) of silver benzotriazole emulsion was obtained.

A preparation of the dispersion of a coupler and a reducing agent is described.

A solution containing 8.8 g of a coupler (Y-1) and 14.3 g of the exemplified compound A-25 of the present invention in 10 ml of tricresyl phosphate and 30 ml of ethyl acetate, was dispersed by emulsification in 110 g of an aqueous 10% by weight gelatin solution containing 1.0 g of sodium dodecylbenzenesulfonate, to prepare the dispersion A of the coupler and the reducing agent.

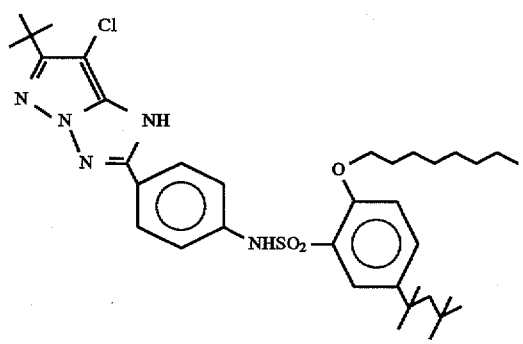

Y-1

Further, dispersions B, C, D, E, F, G, H, I, J, and K were prepared in the same manner as dispersion A of coupler and color-developing agent, except that exemplified compounds (A-3), (A-7), (A-9), (A-5), (A-15), (A-23), (A-27), and (A-32) of the present invention, and comparative compounds (EX-1) and (EX-2) as illustrated below, were used in place of the compound A-25, in equal molar amount, respectively.

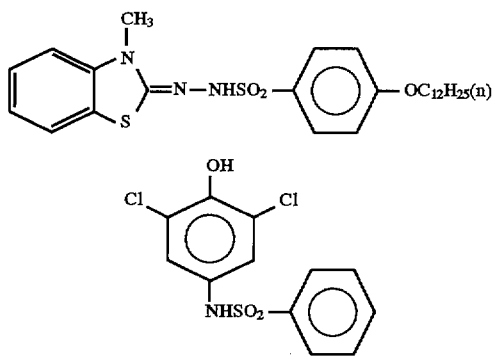

EX-1

EX-2

A support was wet-coated with a coating solution containing 10 g of the silver benzotriazole emulsion, 6 g of a blue-sensitive silver halide emulsion, 10 g of water, and 5 g of urea, as a heat solvent, per 20 g of each of the dispersions A to K of the coupler and the color-developing agent. Then the support was dried, and then it was coated with a gelatin protective layer containing 1% by weight of guanidine trichloroacetic acid, to prepare heat development light-sensitive materials 101 to 111, respectively.

Each of the thus obtained heat development light-sensitive materials was image-wise exposed to light, and heated for 5 seconds at 135° C. After that, the maximum image density at the exposed portion ($D_{max}$), and the fog density at the unexposed portion ($D_{min}$), were measured using an X-RITE 310 densitometer (manufactured by X-RITE Co.).

TABLE 2

| Sample No. | Color Developing Agent | Dispersion | Density of Image Quality after Processing | | Remarks |
|---|---|---|---|---|---|
| | | | Dmin | Dmax | |
| 101 | A-25 | A | 0.16 | 0.97 | Compound according to This Invention |
| 102 | A-3 | B | 0.15 | 0.79 | Compound according to This Invention |
| 103 | A-7 | C | 0.16 | 0.81 | Compound according to This Invention |
| 104 | A-9 | D | 0.17 | 0.77 | Compound according to This Invention |
| 105 | A-5 | E | 0.77 | 0.77 | Compound according to This Invention |
| 106 | A-15 | F | 0.16 | 0.80 | Compound according to This Invention |
| 107 | A-23 | G | 0.15 | 0.93 | Compound according to This Invention |
| 108 | A-27 | H | 0.18 | 0.91 | Compound according to This Invention |
| 109 | A-32 | I | 0.17 | 0.95 | Compound according to This Invention |

TABLE 2-continued

| Sample No. | Color Developing Agent | Dispersion | Density of Image Quality after Processing | | Remarks |
|---|---|---|---|---|---|
| | | | Dmin | Dmax | |
| 110 | EX-1 | J | 0.19 | 0.21 | Comparative Compound |
| 111 | EX-2 | K | 0.17 | 0.22 | Comparative Compound |

It is apparent from the results shown in Table 2 that yellow color formation at the low temperature and rapid processing is remarkably improved by the use of the compound according to the present invention as a color-developing agent for heat development, as compared to the comparative compounds EX-1 and EX-2.

Example 2

Heat development light-sensitive material Samples 201 to 203 were prepared exactly in the same manner as the Sample 101 described in Example 1, except that 6.4 g of a Coupler (M-1), 9.0 g of a Coupler (M-2), and 4.6 g of a Coupler (M-3) were used in place of the Coupler (Y-1), respectively. Further, heat development light-sensitive materials, in which only the coupler of Samples 102 and 103 was replaced as described above, were prepared. That is, Samples 204 to 206 were obtained as modifications of Sample 102, and Samples 207 to 209 were obtained as modifications of Sample 103.

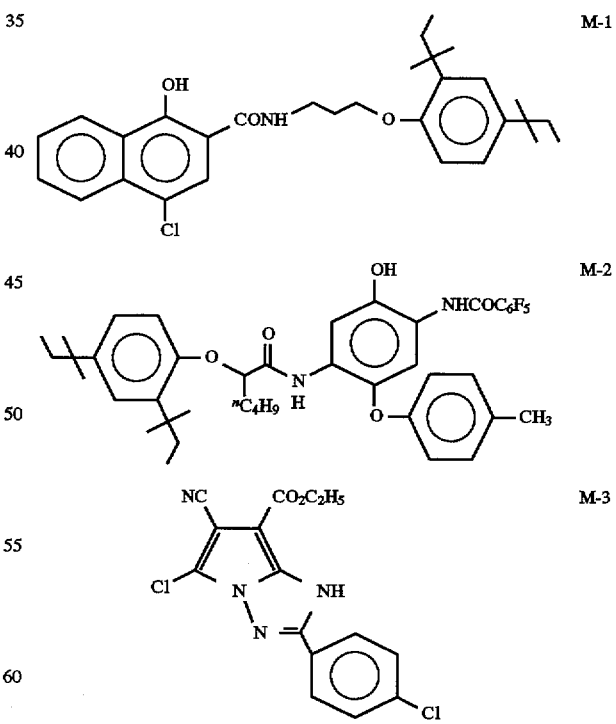

Each of these heat development light-sensitive materials was subjected to exposure followed by heat processing, and then density measurement, in the same manner as in Example 1. The results that were obtained are shown in Table 3.

TABLE 3

| Sample No. | Color Developing Agent/Coupler each used | Density of Image after Processing Dmin | Density of Image after Processing Dmax | Remarks |
|---|---|---|---|---|
| 201 | A-25 /M-1 | 0.16 | 0.88 | Compound according to This Invention |
| 202 | A-25 /M-2 | 0.15 | 0.91 | Compound according to This Invention |
| 203 | A-25 /M-3 | 0.17 | 0.87 | Compound according to This Invention |
| 204 | EX-1 /M-1 | 0.18 | 0.21 | Coparative Compoud |
| 206 | EX-1 /M-2 | 0.16 | 0.19 | Coparative Compoud |
| 207 | EX-1 /M-3 | 0.15 | 0.18 | Coparative Compoud |
| 208 | EX-2 /M-1 | 0.17 | 0.17 | Coparative Compoud |
| 209 | EX-2 /M-2 | 0.18 | 0.20 | Coparative Compoud |
|  | EX-2 /M-3 | 0.17 | 0.19 | Coparative Compoud |

These results indicate that magenta color formation is considerably improved by the use of the color-developing agent A-25 according to the present invention, as compared to the comparative compounds EX-1 and EX-2.

Example 3

Heat development light-sensitive material Sample 301 was prepared exactly in the same manner as Sample 101 described in Example 1, except that 5 g of 2,6-dichloro-4-aminophenol was used in place of the exemplified compound A-25 of the present invention.

After the Samples 101 and 301 were stored for 3 days under conditions of 45° C. and 80% RH., these samples were subjected to exposure and heat development, in the same manner as in Example 1. As a result, almost the same quality of image as in Example 1 was formed in the Sample 101, whereas no image was obtained in the Sample 301. Therefore, it is apparent that the exemplified compound A-25 according to the present invention is superior to 2,6-dichloro-4-aminophenol in terms of storage stability.

Example 4

One surface of a paper support, both surfaces of which had been laminated with polyethylene, was subjected to corona discharging treatment, and a subbing gelatin layer containing sodium dodecylbenzenesulfonate was provided on the surface, and two photographic constructive layers mentioned below were then coated over the subbing layer, to prepare two-layer color photographic paper Sample 401. Coating compositions for the photographic layers were prepared as mentioned below.

Preparation of Coating Composition for the First Layer:

39 g of a Coupler (Y-2), 16.3 g of a Color-developing agent (A-31), and 80 g of a Solvent (Solv-1) were dissolved in ethyl acetate, and the resulting solution was dispersed by emulsification in 400 g of aqueous 16% gelatin solution containing 10% sodium dodecylbenzenesulfonate and citric acid, to prepare an emulsified dispersion A. On the other hand, a silver chlorobromide emulsion A was prepared, which was a mixture (3/7 as silver molar ratio) comprising a large-size emulsion A, of cubic grains having a mean grain size of 0.88 µm, and a small-size emulsion A, of cubic grains having a mean grain size of 0.70 µm. The two emulsions had a fluctuation coefficient of grain size distribution of 0.08 and 0.10, respectively. The two size emulsions each had 0.3 mol % of silver bromide locally on a part of the surface of the grains, which consisted essentially of silver chloride. Each of blue-sensitizing dyes A, B, and C mentioned below was added to the mixture emulsion, in an amount of $1.4 \times 10^{-4}$ mol per mol of silver to the large-size emulsion A, and an amount of $1.7 \times 10^{-4}$ mol per mol of silver to the small-size emulsion A. Then, the mixture emulsion was chemically sensitized with a sulfur sensitizer and a gold sensitizer. The previously prepared emulsified dispersion A and the silver chlorobromide mixture emulsion A were blended, to obtain a coating composition for the first layer, which comprised the components mentioned below. The amount of the emulsion coated indicates the amount of silver therein.

Another coating composition for the second layer was prepared in the similar manner as above. 1-Hydroxy-3,5-dichloro-s-triazine sodium salt was used as the gelatin-hardening agent for each layer.

Each layer contained 15 mg/m² of Cpd-2, 60 mg/m² of Cpd-3, 500 mg/m² of Cpd-4, and 10 mg/m² of Cpd-5.

The following spectral sensitizing dyes were added to the silver chlorobromide emulsions for the first layer.

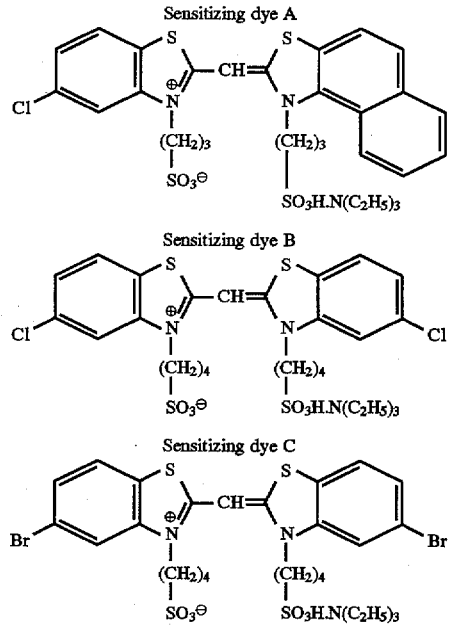

(Both were added, each in an amount of $1.4 \times 10^{-4}$ mol per mol of silver halide to the large-size emulsion, and each in an amount of $1.7 \times 10^{-4}$ mol per mol of silver halide to the small-size emulsion.)

To each of the blue-sensitive emulsion layers was added 1-(5-methylureidophenyl)-5-mercaptotetrazole, in an amount of $3.0 \times 10^{-3}$ mol per mol of silver halide.

Layer Constitution of Photographic Material Samples

The composition of each layer of the photographic material sample is mentioned below. The number indicates the amount of the component coated (g/m²). The amount of the silver halide emulsion coated is represented by the amount of silver therein coated.

| Support | |
|---|---|
| Polyethylene-laminated paper (containing white pigment (TiO₂) and bluish dye (ultramarine) in polyethylene below the first layer) | |
| First Layer | |
| Above-mentioned Silver Chlorobromide Emulsion A | 0.20 |
| Gelatin | 1.50 |
| Yellow Coupler (Y-2) | 0.39 |
| Color-Developing Agent (A-31) | 0.16 |
| Solvent (Solv-1) | 0.80 |
| Second Layer (Protective Layer) | |
| Gelatin | 1.00 |
| Acryl-modified copolymer of polyvinyl alcohol (modification degree 17%) | 0.05 |
| Liquid paraffin | 0.02 |
| Surfactant (Cpd-1) | 0.01 |

Further, Samples 411 to 413 were prepared exactly in the same manner as Sample 401, except that the silver chlorobromide emulsion A in the coating composition for the first layer was replaced by the silver chlorobromide emulsion B mentioned below in the same silver amount, and the coupler was replaced by Magenta Couplers (M-4), (M-5), and (M-6) mentioned below, each in an equimolar amount, respectively.

Silver Chlorobromide Emulsion B: a ⅓ (as silver molar ratio) mixture comprising a large-size emulsion B, of cubic grains having a mean grain size of 0.55 μm, and a small-size emulsion B, of cubic grains having a mean grain size of 0.39 μm; the two emulsions each having a deviation coefficient of grain size distribution of 0.10 and 0.08, respectively, and each having 0.8 mol % of AgBr locally on a part of the surface of the grains consisting essentially of silver chloride.

The following spectral sensitizing dyes were added to the silver chlorobromide emulsion B.

(the sensitizing dye D was added, in an amount of $3.0 \times 10^{-4}$ mol per mol of silver halide to the large-size emulsion, and in an amount of $3.6 \times 10^{-5}$ mol per mol of silver halide to the small-size emulsion; the sensitizing dye E was added, in an amount of $4.0 \times 10^{-5}$ mol per mol of silver halide to the large-size emulsion, and in an amount of $7.0 \times 10^{-5}$ mol per mol of silver halide to the small-size emulsion; and the sensitizing dye F was added, in an amount of $2.0 \times 10^{-4}$ mol per mol of silver halide to the large-size emulsion, and in an amount of $2.8 \times 10^{-4}$ mol per mol of silver halide to the small-size emulsion.)

Sensitizing dye D

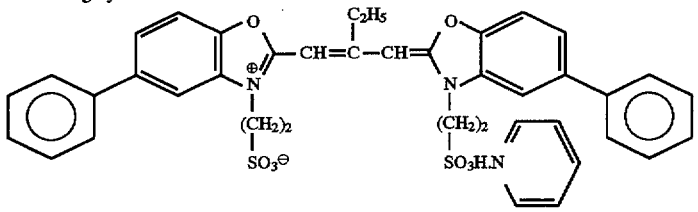

Sensitizing dye E

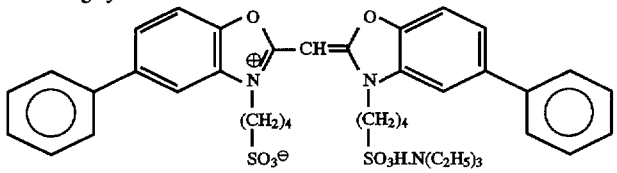

Sensitizing dye F

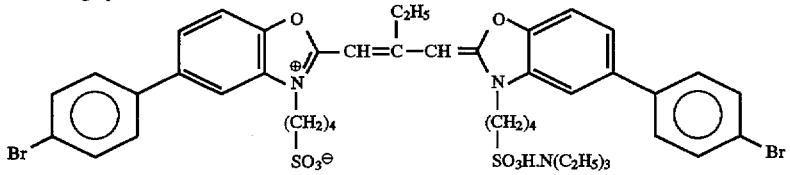

(Y-2)
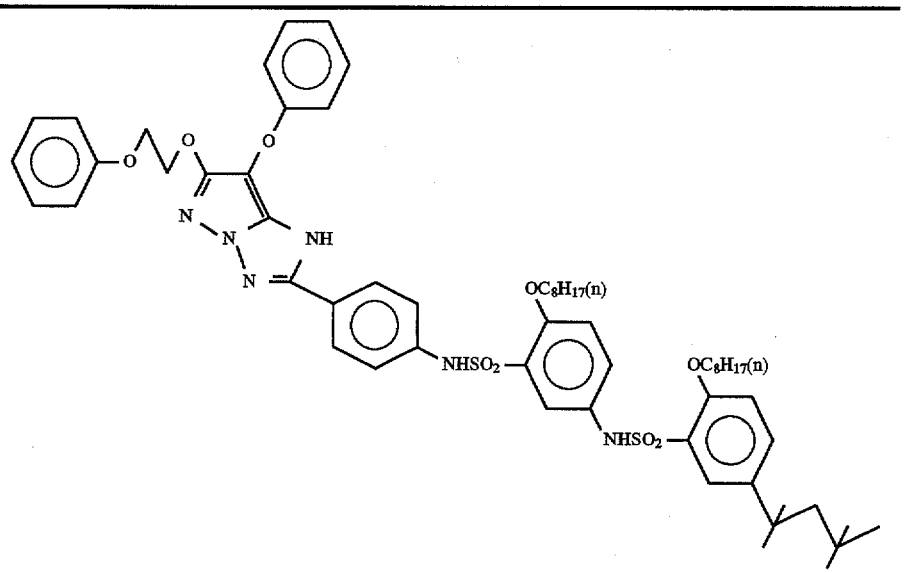
(M-4)
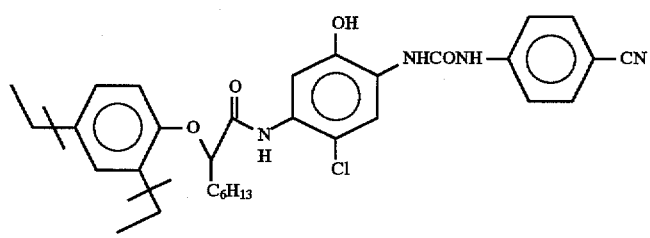
(M-5)
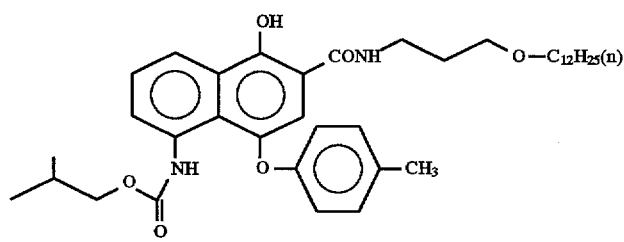
(M-6)
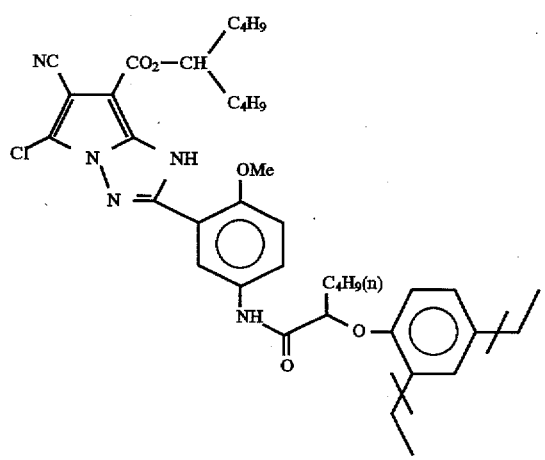
(Solv-1) Solvent
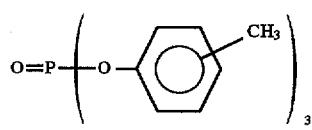

(Cpd-1) 7:3 mixture (by weight ratio) of

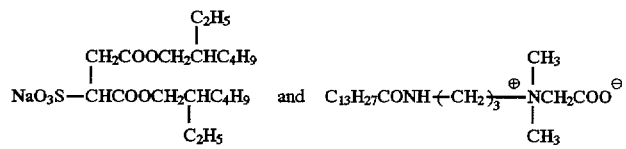

(Cpd-2) Antiseptic

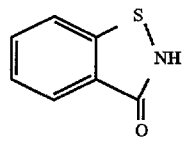

(Cpd-3) Antiseptic

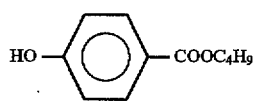

(Cpd-4) Antiseptic

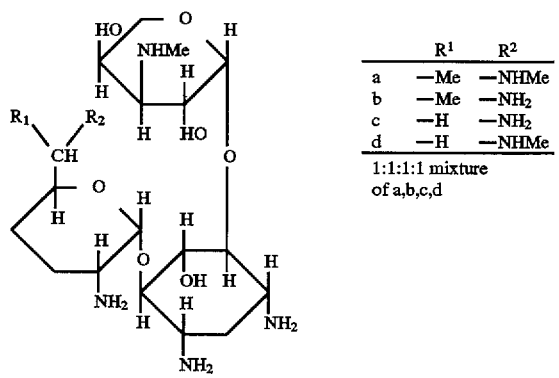

|   | $R^1$ | $R^2$ |
|---|---|---|
| a | —Me | —NHMe |
| b | —Me | —$NH_2$ |
| c | —H | —$NH_2$ |
| d | —H | —NHMe |

1:1:1:1 mixture of a,b,c,d (Cpd-5) Antiseptic

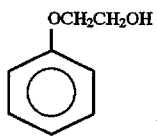

Sample 401 and Samples 411 to 413 thus prepared were subjected to gradient exposure via a sensitometric blue filter and a sensitometric green filter, respectively, by means of a sensitometer (FWH Model, manufactured by Fuji Photo Film Co.; its light source has a color temperature of 3200° K.).

The thus-exposed samples were processed according to the color development process with the processing compositions mentioned below.

| Processing Steps | Temperature | Time |
|---|---|---|
| Color Development | 40° C. | 30 sec. |
| Bleach-Fixation | 40° C. | 45 sec. |
| Rinsing | Room Temperature | 45 sec. |

Color Developer

| | |
|---|---|
| Water | 600 ml |
| Pottasium phosphate | 40 g |
| Disodium-N,N-bis(sulfonatoethyl)hydroxylamine | 10 g |
| KCl | 5 g |
| Hydroxyethylidene-1,1-diphosphonic acid solution (30%) | 4 ml |
| 1-Phenyl-4-methyl-4-hydroxymethyl-3-pyrazolidone | 2 g |
| Water to make | 1000 ml |
| pH (25° C.) (adjusted with pottassium hydroxide) | 12.0 |

Bleach-fixing Solution

| | |
|---|---|
| Water | 600 ml |
| Ammonium thiosulfate (700 g/liter) | 93 ml |
| Ammonium sulfite | 40 ml |
| Ammonium ethylenediaminetetraacetate Iron (III) | 55 g |
| Ethylenediaminetetraacetate | 2 g |

77

-continued

| | |
|---|---|
| Nitric acid (67%) | 30 g |
| Water to make | 1000 ml |
| pH (25° C.) (adjusted with acetic acid and ammonia) | 5.8 |

Rinsing Solution

Deionized water with electric conductivity of 5 μS/cm or less) (pH 6.5) that had been sterilized with a sodium salt of chlorinated isocyanuric acid in advance.

The maximum color density of each of the thus-processed samples was measured through a blue filter for Sample 401, while through a green filter for Samples 411 to 413. The density at a portion of the maximum color formation ($D_{max}$) is shown in Table 4.

TABLE 4

| Sample No. | Coupler used | Dmax |
|---|---|---|
| 401 | Y-2 | 2.1 |
| 411 | M-4 | 2.0 |
| 412 | M-5 | 2.2 |
| 413 | M-6 | 1.9 |

As is apparent from the results shown in Table 4, a satisfactory color density can be obtained by the use of the compound according to the present invention in a short processing time.

78

Example 5

10.9 g of a Coupler (Y-3) was weighed and dissolved in 16.1 g of a high-boiling-point organic solvent (dibutylphthalate) and 24 ml of ethyl acetate. The resulting solution was dispersed by emulsification in 200 g of an aqueous 10 wt % gelatin solution containing 1.5 g of sodium dodecylbenzenesulfonate.

The whole quantity of the thus obtained emulsion dispersion was added to 247 g of a silver chlorobromide emulsion (with 70.0 g of silver per kg of emulsion, and a silver bromide content of 70 mol %). The resulting emulsion was coated on a subbing layer applied on a triacetate film base, in an amount of 1.73 g/m² in terms of coated silver. Further, a gelatin layer (protective layer) was coated on the above-mentioned emulsion layer, in a film thickness (dry) of 1.0 μm, to prepare a Sample 501. 1-Hydroxy-3,5-dichloro-s-triazine sodium salt was used as the gelatin hardener for each layer.

Additionally, Samples 511, 512, and 513 were prepared exactly in the same manner as Sample 501, except that Couplers (M-7), (M-8), and (M-9) were used in replace with the Coupler (Y-3), in an equimolar amount, respectively.

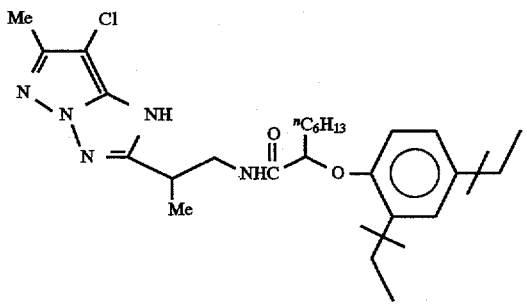

Y-3

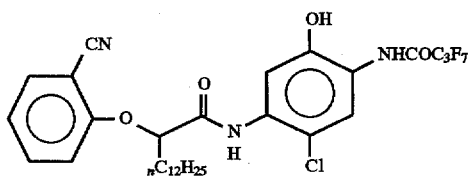

M-7

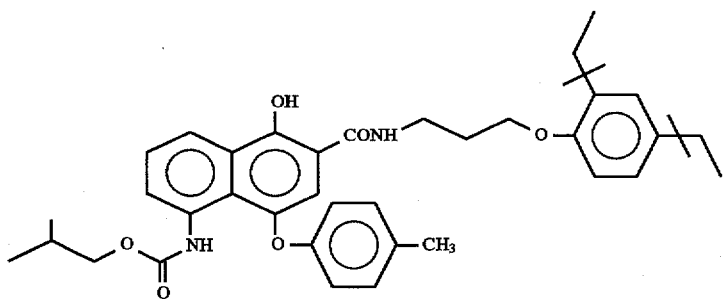

M-8

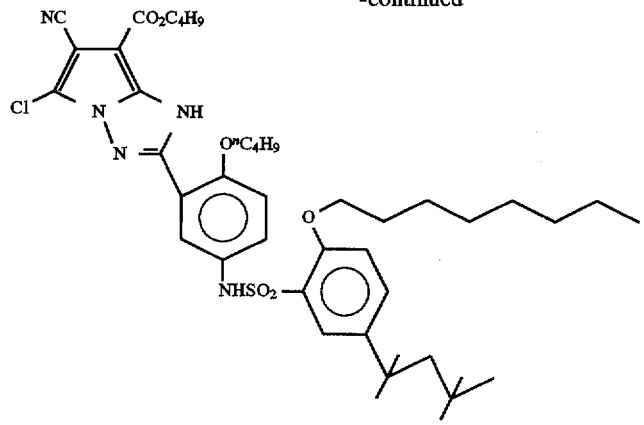

M-9

The thus prepared color photographic light-sensitive material Sample 501 was image-wise exposed to light and then processed according to the following process.

Process for Color Development

| Processing Steps | Time | Temperature |
|---|---|---|
| Color Development | 3 min. 15 sec. | 38° C. |
| Bleaching | 3 min. 00 sec. | 38° C. |
| Washing | 30 sec. | 24° C. |
| Fixing | 3 min. 00 sec. | 38° C. |
| Washing (1) | 30 sec. | 24° C. |
| Washing (2) | 30 sec. | 24° C. |
| Stabilization | 30 sec. | 38° C. |
| Drying | 4 min. 20 sec. | 55° C. |

The compositions of the processing liquids are described below.

| Color Developer | |
|---|---|
| Diethylenetriamine-pentaacetic acid | 1.0 g |
| 1-Hydroxyethylidene-1,1-diphosphonic acid | 2.0 g |
| Sodium sulfite | 4.0 g |
| Potasium carbonate | 30.0 g |
| Potasium bromide | 1.4 g |
| Potassium iodide | 1.5 mg |
| Hydroxylamine sulfate salt | 2.4 g |
| Developing Agent according to this Invention (A-46) | 20 mmol |
| Water to make | 1 liter |
| pH (adjusted with potassium hydroxide and sulfuric acid) | 10.05 |

| Bleaching Solution | (Unit g) |
|---|---|
| Sodium Ethylenediaminetetraacetate Fe(III) trihydrate | 100.0 |
| Disodium ethylenediaminetetraacetate | 10.0 |
| 3-Mercapto-1,2,4-triazole | 0.03 |
| Ammonium bromide | 140.0 |
| Ammonium nitrate | 30.0 |
| Aqueous ammonia (27%) | 6.5 milliliter |
| Water to make | 1.0 liter |
| pH (adjusted with aqueous ammonia and nitric acid) | 6.0 |

| Fixing Solution | (Unit g) |
|---|---|
| Disodium ethylenediaminetetraacetate | 0.5 |
| Ammonium sulfite | 20.0 |
| Ammonium thiosulfate aqueous solution (700 g/liter) | 295.0 milliliter |
| Acetic acid (90%) | 3.3 |
| Water to make | 1.0 liter |
| pH (adjusted with aqueous ammonia and acetic acid) | 6.7 |

| Stabilizer | (Unit g) |
|---|---|
| p-Nonylphenoxypolyglycidol (average polymerization degree of glycidol: 10) | 0.2 |
| Ethylenediaminetetraacetic acid | 0.05 |
| 1,2,4-Triazole | 1.3 |
| 1,4-Bis(1,2,4-triazole-1-yl methyl)piperazine | 0.75 |
| Hydroxyacetic acid | 0.02 |
| Hydroxyethylcellulose (HEC SP-2000, trade name; manufactured by Daicel Chemical Industries Ltd.) | 0.1 |
| 1,2-Benzisothiazoline-3-one | 0.05 |
| Water to make | 1.0 liter |
| pH | 8.5 |

The maximum density of the yellow image obtained by processing Sample 501 as mentioned above was measured. Additionally, the same test was repeated, except that an equimolar amount of the compound (A-43) according to the present invention was added to a developer in place of the compound (A-46) according to the present invention incorporated in the developer. Still further, the same tests were also repeated with respect to Samples 511 to 513. As a result, a yellow image was obtained by Sample 501, whereas a magenta image was obtained by Samples 511, 512, and 513, respectively. The maximum density of each of these samples was also measured. The results obtained are shown in Table 5.

TABLE 5

| Sample No. | Coupler used | Dmax Color Developing Agent used | |
|---|---|---|---|
| | | A-46 | A-43 |
| 501 | Y-3 | 2.0 | 1.8 |
| 511 | M-7 | 1.9 | 2.0 |
| 512 | M-8 | 1.9 | 2.1 |
| 513 | M-9 | 2.1 | 2.1 |

As is apparent from the results shown in Table 5, a satisfactory color density can be obtained by the use of the color developer containing the compound according to the present invention.

Example 6

Samples 601 and 611 to 613 were prepared exactly in the same manner as Sample 401 prepared in Example 4, except that no color-developing agent was incorporated in any of the samples, and the coupler was replaced with the couplers shown in Table 6, in an equimolar amount. With respect to a silver chlorobromide emulsion to be used in these samples, the silver chlorobromide emulsion A used in Example 4 was employed for Sample 601, whereas the silver chlorobromide emulsion B used in Example 4 was employed for Samples 611 to 613.

TABLE 6

| Sample No. | Coupler |
|---|---|
| 601 | Y-4 |
| 611 | M-10 |
| 612 | M-11 |
| 613 | M-12 |

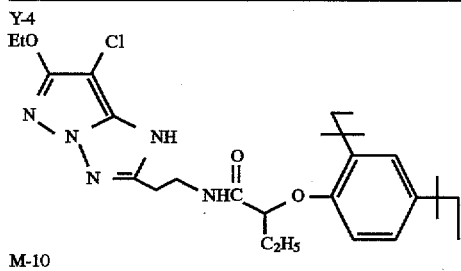

M-10

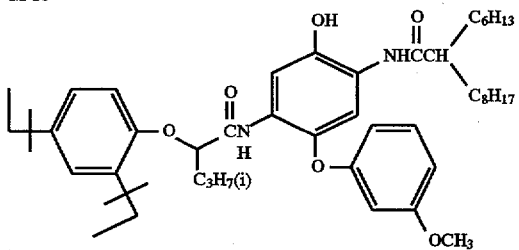

M-11

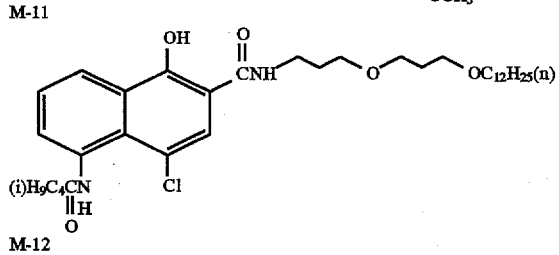

M-12

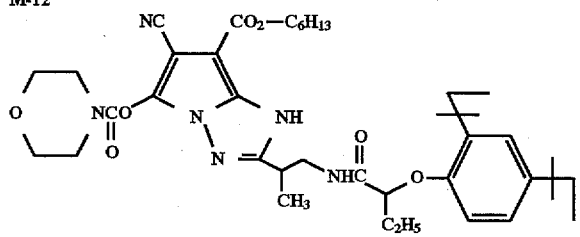

By using an FWH-type sensitometer (color temperature of the light source: 3,200° K.), manufactured by Fuji Photo Film Co., Ltd., gradation exposure was given to the thus prepared Sample (601) through a blue filter for sensitometry, to the thus prepared Samples (611) to (613) through a green filter for sensitometry.

The thus exposed Samples were processed with the following processing solutions in the following processing steps:

| Processing step | Temperature | Time |
|---|---|---|
| Development | 40° C. | 45 sec |
| Bleach-fix | 40° C. | 45 sec |
| Rinse | room temperature | 45 sec |
| (Developing Solution) | | |
| Water | | 800 ml |
| Potassium phosphate | | 40 g |
| Disodium N,N-bis(sulfonatoethyl)hydroxylamine | | 10 g |
| KCl | | 5 g |
| Hydroxylethylidene-1,1-diphosphonic acid (30 | | 4 ml |
| Color developing agent (A-42) | | 2.4 g |
| Water to make | | 1,000 ml |
| pH (at 25 0C by using potassium hydroxide) | | 12 |
| (Bleach-fix Solution) | | |
| Water | | 600 ml |
| Sodium thiosulfate (700 g/liter) | | 93 ml |
| Sodium sulfite | | 40 ml |
| Ethylenediaminetetraacetic acid iron (III) ammonium salt | | 55 g |
| Ethylenediamintetraacetic acid | | 2 g |
| Nitric acid (67 | | 30 g |
| Water to make | | 1,000 ml |
| pH (at 25 0C by using acetic acid and ammonia water) | | 5.8 |
| (Rinsing Solution) | | |
| Sodium chlorinated-isocyanurate | | 0.02 g |
| Deionized water (conductivity: 5 μS/cm or below) | | 1,000 ml |
| pH | | 65 |

Samples 601 and 611 to 613 were processed exactly according to the above-described processing steps, except that the color-developing agent (A-42) contained in a developer was replaced by the compound (A-46), in an equimolar amount.

As a result, a satisfactory color density can be obtained.

Having described our invention as related to the present embodiments, it is our intention that the invention not be limited by any of the details of the description, unless otherwise specified, but rather be construed broadly within its spirit and scope as set out in the accompanying claims.

What is claimed:

1. A method for forming an image, comprising developing a silver halide photographic light-sensitive material in the presence of a compound represented by general formula (A):

general formula (A)

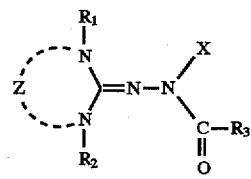

wherein $R_1$ and $R_2$ each represent an alkyl group, an aryl group, or a heterocyclic group; X represents a hydrogen atom, an acyl group, or a sulfonyl group; Z represents two or more non-metal atoms necessary to complete a 5- or 6-membered heterocyclic nucleus; and $R_3$ represents an alkyl group, an aryl group, a heterocyclic group, —$OR_4$, or —$NR_5R_6$, wherein $R_4$, $R_5$, and $R_6$ each represent an alkyl group, an aryl group, or a heterocyclic group, with the proviso that $R_6$ may be a hydrogen atom.

2. The method for forming an image as claimed in claim 1, wherein the silver halide photographic light-sensitive material exposed to light imagewise is subjected to development processing with a processing composition containing the compound of general formula (A).

3. The method for forming an image as claimed in claim 1, wherein the silver halide photographic light-sensitive material contains the compound of general formula (A).

4. The method for forming an image as claimed in claim 1, wherein the compound of general formula (A) forms an oxidation product at a portion where, in the light-sensitive material, a latent image formed by an image-wise exposure to light is present, the oxidation product being capable of forming a dye image by reaction with a coupler.

5. The method for forming an image as claimed in claim 1, wherein, in general formula (A), $R_1$ and $R_2$ each represent an alkyl group having from 1 to 10 carbon atoms, which is unsubstituted or substituted with one or more substituents selected from a halogen atom, a hydroxy group, an alkoxy group, a carboxy group, and a sulfo group.

6. The method for forming an image as claimed in claim 1, wherein, in general formula (A), $R_3$ represents an alkyl group having from 1 to 32 carbon atoms, which is unsubstituted or substituted with one or more substituents; an aryl group having from 6 to 10 carbon atoms, which is unsubstituted or substituted with one or more substituents; —$OR_4$, or —$NR_5R_6$.

7. The method for forming an image as claimed in claim 1, wherein, in general formula (A), X represents a hydrogen atom, an acyl group having from 2 to 5 carbon atoms, which is unsubstituted or substituted with a halogen atom, a hydroxy group, an alkoxy group, a carboxy group, or a sulfo group; an alkylsulfonyl group having from 1 to 4 carbon atoms, or a benzenesulfonyl group.

8. The method for forming an image as claimed in claim 1, wherein, in general formula (A), Z represents non-metal atoms necessary to complete an imidazole nucleus, a benzimidazole nucleus, an ethyleneurea nucleus, or a tetrahydropyrimidone nucleus, each of which hetero ring may be unsubstituted or substituted with a substituent.

9. A silver halide photographic light-sensitive material, comprising a compound represented by general formula (A):

general formula (A)

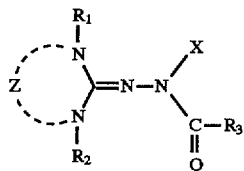

wherein $R_1$ and $R_2$ each represent an alkyl group, an aryl group, or a heterocyclic group; X represents a hydrogen atom, an acyl group, or a sulfonyl group; Z represents two or more non-metal atoms necessary to complete a 5- or 6-membered heterocyclic nucleus; and $R_3$ represents an alkyl group, an aryl group, a heterocyclic group, —$OR_4$, or —$NR_5R_6$, wherein $R_4$, $R_5$, and $R_6$ each represent an alkyl group, an aryl group, or a heterocyclic group, with the proviso that $R_6$ may be a hydrogen atom.

10. The silver halide photographic light-sensitive material as claimed in claim 9, wherein the light-sensitive material is a silver halide photothermography light-sensitive material, and wherein the compound of general formula (A) forms an oxidation product at the portion where, in the light-sensitive material, a latent image formed by an image-wise exposure to light is present, the oxidation product being capable of forming a dye image by reaction with a coupler.

11. The silver halide photographic light-sensitive material as claimed in claim 9, wherein the light-sensitive material is capable of forming an image by an activator processing, and wherein the compound of general formula (A) forms an oxidation product at the portion where, in the light-sensitive material, a latent image formed by an image-wise exposure to light is present, the oxidation product being capable of forming a dye image by reaction with a coupler.

12. The silver halide photographic light-sensitive material as claimed in claim 9, wherein the compound of general formula (A) forms an oxidation product at the portion where, in the light-sensitive material, a latent image formed by an image-wise exposure to light is present, the oxidation product being capable of forming a dye image by reaction with a coupler.

13. The silver halide photographic light-sensitive material as claimed in claim 9, wherein, in general formula (A), $R_1$ and $R_2$ each represent an alkyl group having from 1 to 10 carbon atoms, which is unsubstituted or substituted with one or more substituents selected from a halogen atom, a hydroxy group, an alkoxy group, a carboxy group, and a sulfo group.

14. The silver halide photographic light-sensitive material as claimed in claim 9, wherein, in general formula (A), $R_3$ represents an alkyl group having from 1 to 32 carbon atoms, which is unsubstituted or substituted with one or more substituents; an aryl group having from 6 to 10 carbon atoms, which is unsubstituted or substituted with one or more substituents; —$OR_4$, or —$NR_5R_6$.

15. The silver halide photographic light-sensitive material as claimed in claim 9, wherein, in general formula (A), X represents a hydrogen atom, an acyl group having from 2 to 5 carbon atoms, which is unsubstituted or substituted with a halogen atom, a hydroxy group, an alkoxy group, a carboxy group, or a sulfo group; an alkylsulfonyl group having from 1 to 4 carbon atoms, or a benzenesulfonyl group.

16. The silver halide photographic light-sensitive material as claimed in claim 9, wherein, in general formula (A), Z represents non-metal atoms necessary to complete an imidazole nucleus, a benzimidazole nucleus, an ethyleneurea nucleus, or a tetrahydropyrimidone nucleus, each of which hetero ring may be unsubstituted or substituted with a substituent.

* * * * *